US012676215B2

(12) United States Patent
Ahmad Zabidi et al.

(10) Patent No.: US 12,676,215 B2
(45) Date of Patent: Jul. 7, 2026

(54) MODEL ROUTING AND ROBUST OUTLIER DETECTION

(71) Applicants: Genentech, Inc., South San Francisco, CA (US); Hoffmann-La Roche Inc., Little Falls, NJ (US)

(72) Inventors: Muhammad Mamduh Bin Ahmad Zabidi, Subang Jaya (MY); Nandini Chitale, Cupertino, CA (US); Michael Paul Dandrea, South San Francisco, CA (US)

(73) Assignees: Genentech, Inc., South San Francisco, CA (US); Hoffmann-La Roche Inc., Little Falls, NJ (US)

( * ) Notice: Subject to any disclaimer, the term of this patent is extended or adjusted under 35 U.S.C. 154(b) by 56 days.

(21) Appl. No.: 18/611,545

(22) Filed: Mar. 20, 2024

(65) Prior Publication Data

US 2024/0233888 A1 Jul. 11, 2024

Related U.S. Application Data

(63) Continuation of application No. PCT/US2022/044152, filed on Sep. 20, 2022.

(Continued)

(51) Int. Cl.
*G16H 10/20* (2018.01)
*G06F 3/0482* (2013.01)
(52) U.S. Cl.
CPC ........... *G16H 10/20* (2018.01); *G06F 3/0482* (2013.01)
(58) Field of Classification Search
CPC ........ G16H 10/20; G06H 10/40; G06H 10/60; G06F 3/0482
See application file for complete search history.

(56) References Cited

U.S. PATENT DOCUMENTS

2006/0173663 A1* 8/2006 Langheier .............. G16H 50/20
                                                      703/11
2017/0236060 A1 8/2017 Ignatyev
                    (Continued)

FOREIGN PATENT DOCUMENTS

WO WO-2021155329 A1 * 8/2021 ....... G06Q 10/06315

OTHER PUBLICATIONS

Boulesteix et al., Towards evidence-based computational statistics: lessons from clinical research on the role and design of real-data benchmark studies, Sep. 9, 2017, BMC Medical Research Methodology, vol. 17, No. 138, pp. 1-12. (Year: 2017).*

(Continued)

*Primary Examiner* — Christopher L Gilligan
(74) *Attorney, Agent, or Firm* — MORRISON & FOERSTER LLP

(57) ABSTRACT

In one embodiment, a method includes receiving, via graphical user interface of a clinical study tool, a user input including one or more user selected sub-categories from one or more categories associated with a clinical study; selecting, for each clinical-study metric of a plurality of clinical-study metrics, a model from either a baseline model or one of a plurality of category-specific machine-learning models to predict the clinical-study metric using a model performance lookup table; predicting values for the plurality of clinical-study metrics using corresponding selected models; generating one or more predictions for assessing the clinical study based on the predicted values for the plurality of clinical-study metrics; and displaying, via the graphical user interface of the clinical study tool, the one or more predictions for assessing the clinical study.

20 Claims, 26 Drawing Sheets

Related U.S. Application Data

(60)   Provisional application No. 63/246,638, filed on Sep. 21, 2021.

(56)                 References Cited

U.S. PATENT DOCUMENTS

| | | | | |
|---|---|---|---|---|
| 2020/0094824 | A1* | 3/2020 | Schulter | G06F 30/20 |
| 2020/0365229 | A1* | 11/2020 | Fields | G06F 16/285 |
| 2020/0410614 | A1* | 12/2020 | Bonageri | G16H 20/10 |
| 2021/0110313 | A1 | 4/2021 | Jones | |
| 2021/0142904 | A1* | 5/2021 | Michuda | G16H 50/20 |
| 2021/0225463 | A1* | 7/2021 | Knighton, Jr. | G06N 3/045 |
| 2021/0375459 | A1* | 12/2021 | Longmire | G16H 10/60 |

OTHER PUBLICATIONS

Hettige et al., Temporal Cascade and Structural Modelling of EHRs for Granular Readmission Prediction, Feb. 4, 2021, arXiv:2102. 02586v1, pp. 1-9. (Year: 2021).*

International Preliminary Report on Patentability, issued Mar. 26, 2024, for PCT Application No. PCT/US2022/044152, filed Sep. 20, 2022, 7 pages.

International Search Report and Written Opinion, mailed Jan. 2, 2023, for PCT Application No. PCT/US2022/044152, filed Sep. 20, 2022, 9 pages.

* cited by examiner

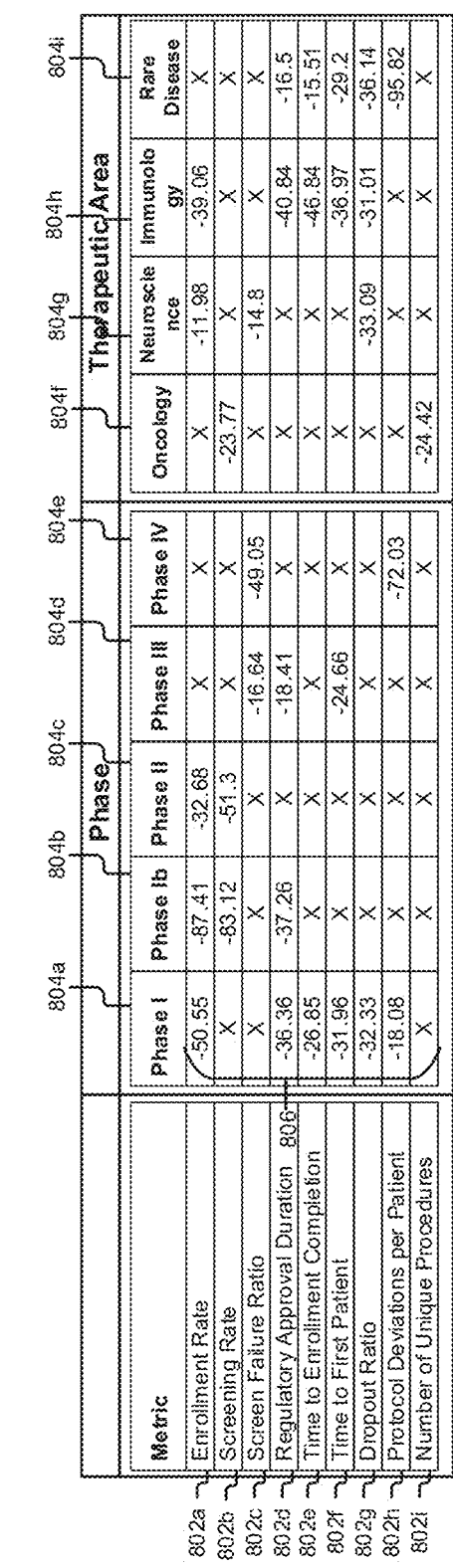

| Metric | Phase | | | | | Therapeutic Area | | | |
| | Phase I | Phase Ib | Phase II | Phase III | Phase IV | Oncology | Neuroscience | Immunology | Rare Disease |
|---|---|---|---|---|---|---|---|---|---|
| Enrollment Rate | -50.55 | -87.41 | -32.68 | X | X | X | -11.98 | -39.06 | X |
| Screening Rate | X | -83.12 | -51.3 | X | X | -23.77 | X | X | X |
| Screen Failure Ratio | X | X | X | -16.64 | -49.05 | X | -14.8 | X | X |
| Regulatory Approval Duration | -36.36 | -37.26 | X | -18.41 | X | X | X | -40.84 | -16.5 |
| Time to Enrollment Completion | -26.85 | X | X | X | X | X | X | -46.84 | -15.51 |
| Time to First Patient | -31.96 | X | X | -24.66 | X | X | X | -36.97 | -29.2 |
| Dropout Ratio | -32.33 | X | X | X | X | X | -33.09 | -31.01 | -36.14 |
| Protocol Deviations per Patient | -18.08 | X | X | X | -72.03 | X | X | X | -95.82 |
| Number of Unique Procedures | X | X | X | X | X | -24.42 | X | X | X |

FIG. 8

| Clinical-study Metrics | Root mean square error (RMSE) associated with baseline model (without outlier method applied) | Root mean square error (RMSE) associated with baseline model (with outlier method applied) |
|---|---|---|
| Metric 1 | 11.93140179 | 11.93140179 |
| Metric 2 | 0.0392123811 | 0.03921191502 |
| Metric 3 | 0.2735980074 | 0.2735359315 |
| Metric 4 | 57.52637113 | 52.64095006 |
| Metric 5 | 413.8380769 | 413.8435105 |
| Metric 6 | 78.4320642 | 72.907326 |
| Metric 7 | 0.1802249641 | 0.1815567557 |
| Metric 8 | 18.87936972 | 16.43780227 |
| Metric 9 | 40.12287268 | 16.439723 |

| Clinical-study Metrics | Percent Data Loss Compared to Z Scores | Modified Z Score Threshold |
|---|---|---|
| Metric 1 | 0.009873060648801129 | 37.5 |
| Metric 2 | 0.00982800928009828 | 13.5 |
| Metric 3 | 0.0006788866259334691 | 3.5 |
| Metric 4 | 0.00728862973760329 | 6.5 |
| Metric 5 | 0.0 | 3.5 |
| Metric 6 | 0.00927734375 | 5.5 |
| Metric 7 | 0.0 | 16.5 |
| Metric 8 | 0.0 | 3.5 |
| Metric 9 | 0.0 | 3.5 |

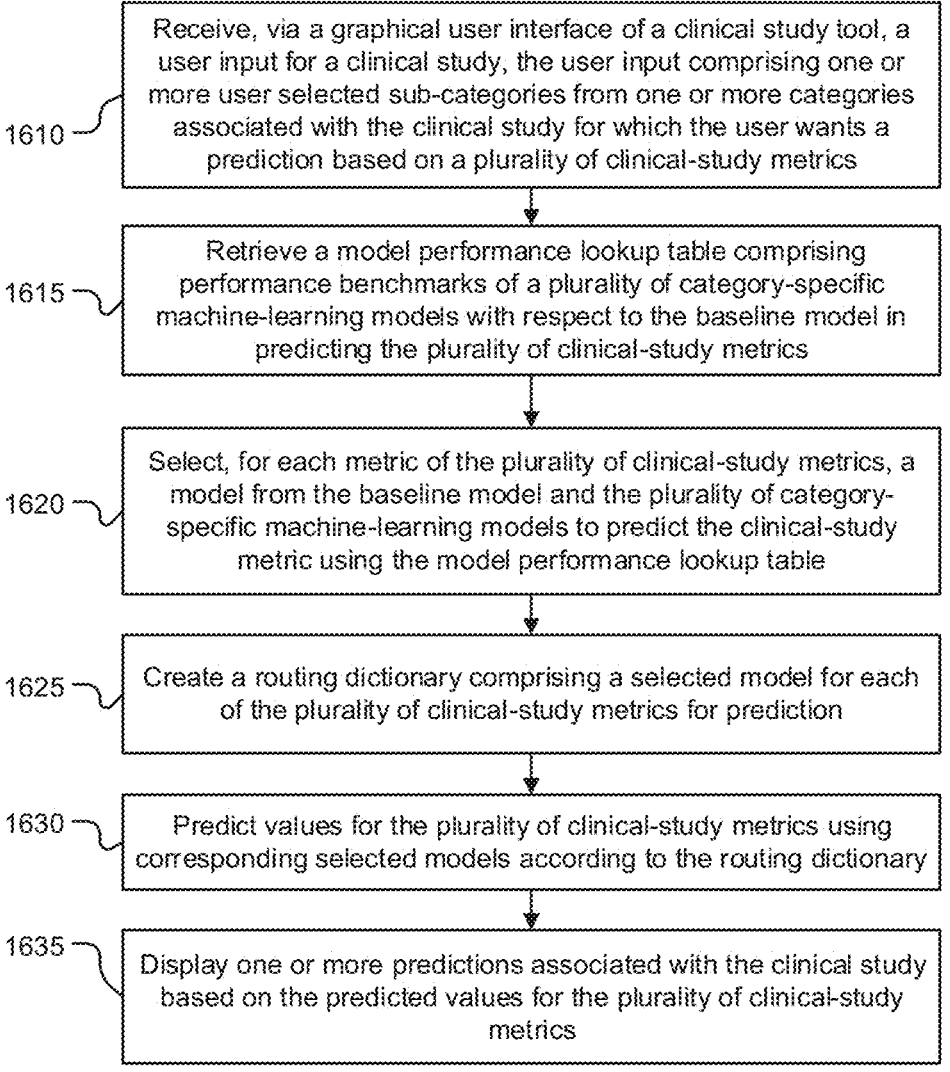

1610 — Receive, via a graphical user interface of a clinical study tool, a user input for a clinical study, the user input comprising one or more user selected sub-categories from one or more categories associated with the clinical study for which the user wants a prediction based on a plurality of clinical-study metrics 1615 — Retrieve a model performance lookup table comprising performance benchmarks of a plurality of category-specific machine-learning models with respect to the baseline model in predicting the plurality of clinical-study metrics 1620 — Select, for each metric of the plurality of clinical-study metrics, a model from the baseline model and the plurality of category-specific machine-learning models to predict the clinical-study metric using the model performance lookup table 1625 — Create a routing dictionary comprising a selected model for each of the plurality of clinical-study metrics for prediction 1630 — Predict values for the plurality of clinical-study metrics using corresponding selected models according to the routing dictionary 1635 — Display one or more predictions associated with the clinical study based on the predicted values for the plurality of clinical-study metrics

FIG. 16

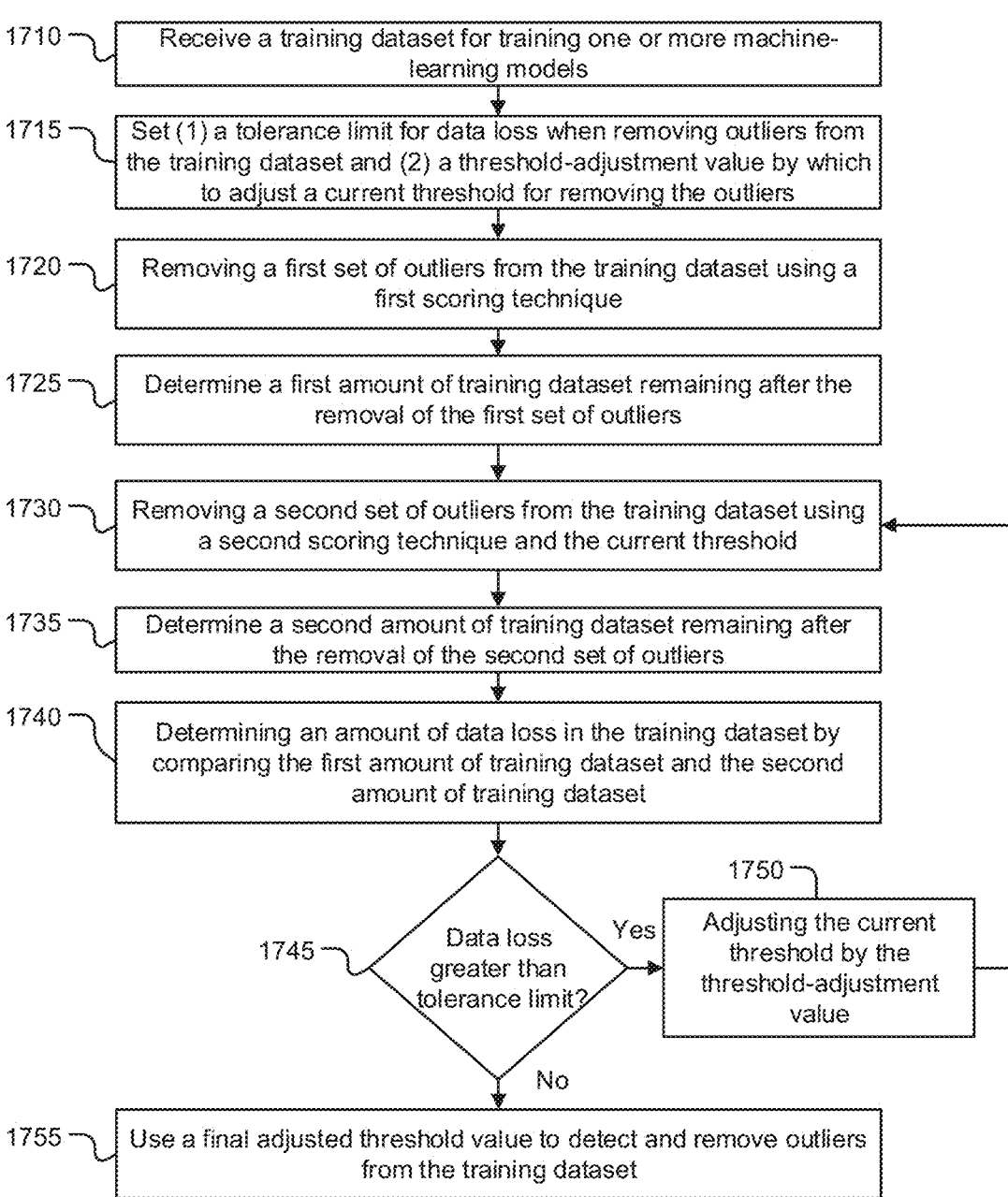

1700

1710 — Receive a training dataset for training one or more machine-learning models 1715 — Set (1) a tolerance limit for data loss when removing outliers from the training dataset and (2) a threshold-adjustment value by which to adjust a current threshold for removing the outliers 1720 — Removing a first set of outliers from the training dataset using a first scoring technique 1725 — Determine a first amount of training dataset remaining after the removal of the first set of outliers 1730 — Removing a second set of outliers from the training dataset using a second scoring technique and the current threshold 1735 — Determine a second amount of training dataset remaining after the removal of the second set of outliers 1740 — Determining an amount of data loss in the training dataset by comparing the first amount of training dataset and the second amount of training dataset 1745 — Data loss greater than tolerance limit?

Yes

1750 — Adjusting the current threshold by the threshold-adjustment value

No

1755 — Use a final adjusted threshold value to detect and remove outliers from the training dataset

*FIG. 17*

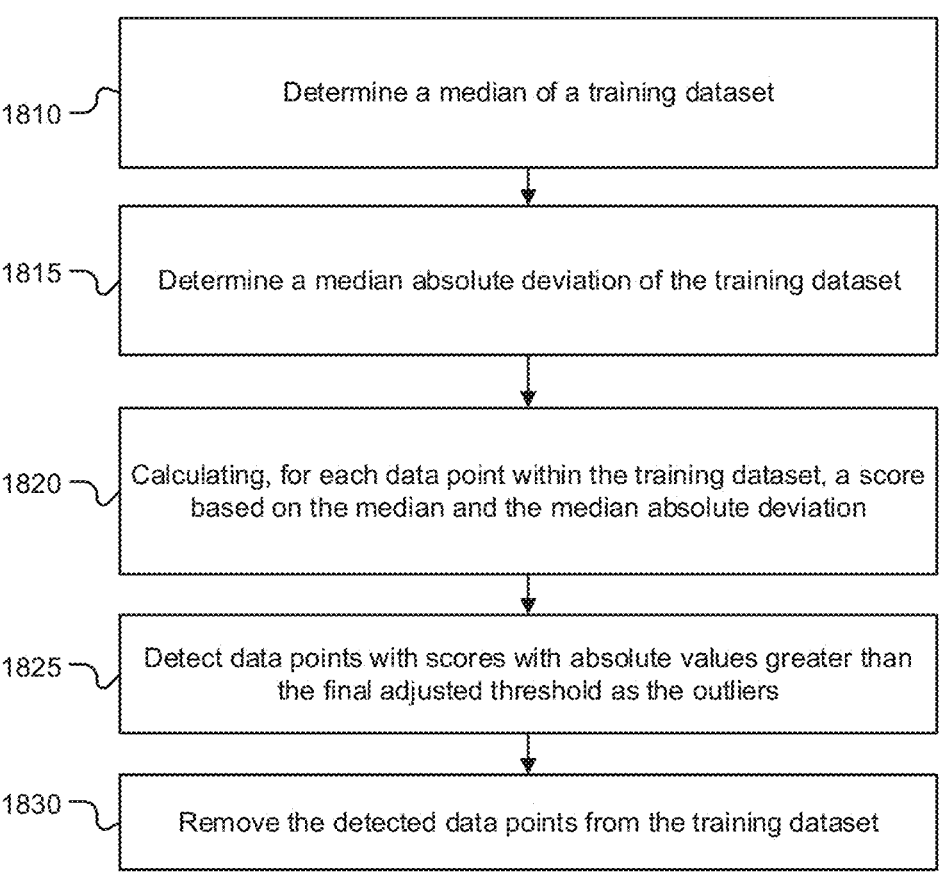

1800

1810 — Determine a median of a training dataset

1815 — Determine a median absolute deviation of the training dataset

1820 — Calculating, for each data point within the training dataset, a score based on the median and the median absolute deviation 1825 — Detect data points with scores with absolute values greater than the final adjusted threshold as the outliers 1830 — Remove the detected data points from the training dataset

*FIG. 18*

MODEL ROUTING AND ROBUST OUTLIER DETECTION

CROSS-REFERENCE TO RELATED APPLICATION

This application is a continuation of International Application No. PCT/US2022/044152, filed on Sep. 20, 2022, which claims the benefit of U.S. Provisional Application No. 63/246,638, filed Sep. 21, 2021, the contents of which are incorporated herein by reference in its entirety for all purposes.

TECHNICAL FIELD

This disclosure generally relates to model routing and robust outlier detection. In particular, the disclosure relates to using model routing to predict a plurality of clinical-study metrics for a clinical study and removing outliers from a training dataset for a machine learning model using an adaptive threshold.

BACKGROUND

A user (e.g., a clinical scientist) may design various protocols or studies that describe patient data associated with a set of clinical-study metrics, such as enrollment rate of patients per month, screening rate of patients per month, a screen failure ratio, a patient dropout ratio, etc. These studies or protocols may be designed for various categories associated with a clinical study or trial, such as for different phases of the clinical trial (e.g., phase 1 study, phase 2 study, etc.) and for different therapeutic areas (e.g., oncology, neurology, ophthalmology, dermatology, etc.).

SUMMARY OF PARTICULAR EMBODIMENTS

A protocol designing phase may be greatly improved or optimized if one or more machine learning (ML) models are trained to predict each of a set of clinical-study metrics for each category associated with a clinical study or trial. Particular embodiments train multiple fine-grained machine-learning models for different categories (e.g., different phases of a clinical trial, different therapeutic areas (TAs)) of a dataset, instead of one generic model, and describe a model routing algorithm that efficiently selects a correct fine-grained model at inference or run time to make a prediction on a user input associated with a clinical study. To train these fine-grained machine-learning models, a training dataset is filtered or sliced by each category, for example, by phase or by TA, and then a category-specific model is separately trained or built for each category (e.g., for each phase study, for each therapeutic area). Also, a generic or a baseline model is trained based on the whole training dataset without filtering. Then performance of these trained models, including the baseline model and the different category-specific models, during testing are stored in a model performance lookup table. The trained machine-learning models (including the baseline model and the different category-specific models) and the model routing algorithm to select an appropriate model from these trained models may be used in a clinical-study tool (e.g., a tool used by clinical scientists for evaluating or assessing clinical studies and/or conducting clinical trials) for making various predictions on a new clinical study. For example, given various user inputs via a graphical user interface of a clinical study tool, such as selection of a therapeutic area, a study phase, a clinical-study metric, etc., the model routing algorithm may select an appropriate trained model for predicting values for that clinical-study metric. The selected model by the model routing algorithm may output a prediction for an enrollment rate (e.g., patients/month) metric. Similarly, different models may be selected for predicting other clinical-study metrics, such as screening rate of patients, a screen failure ratio, a patient dropout ratio, etc. Using the predicted values by the models for the clinical-study metrics, predictions or data driven insights, such as operational burden measures, site burden measures, patient burden measures, etc. may be generated for display on a graphical user interface of the clinical-study tool. Users (e.g., clinical scientists) may use these predictions during a protocol designing phase to design patient and investigator centric protocols.

When training a machine-learning model (e.g., a baseline model, a category-specific model) using a training dataset, outliers in the training dataset may reduce the quality of the model's predictions. As such, a pre-processing step before training a model may be required to remove outliers in the training dataset. Particular embodiments provide an improved method for data-loss-conscious outlier detection and removal. Instead of arbitrarily changing the threshold for outlier detection, the improved method iteratively increases the threshold, and checks how much data would be lost compared to using a standard method (e.g., using standard z scores). If the amount of data lost is considered unacceptable or more than an acceptable limit (e.g., loss of more than 1% of the dataset), the threshold is increased by a small amount, and the process is repeated until the amount of data lost is within the acceptable limit. The improved method allows for more robust detection of outliers (e.g., to prevent extreme values from obscuring less-extreme values that should still be removed), and also for programmatically setting a threshold that prevents excessive data loss from outlier removal. By properly removing true outliers while including all non-outlier data, the improved method, when used to pre-process a training dataset, improves the predictions of the model trained on this dataset.

The embodiments disclosed herein are only examples, and the scope of this disclosure is not limited to them. Particular embodiments may include all, some, or none of the components, elements, features, functions, operations, or steps of the embodiments disclosed herein. Embodiments according to the invention are in particular disclosed in the attached claims directed to a method, a storage medium, a system and a computer program product, wherein any feature mentioned in one claim category, e.g., method, can be claimed in another claim category, e.g., system, as well. The dependencies or references back in the attached claims are chosen for formal reasons only. However any subject matter resulting from a deliberate reference back to any previous claims (in particular multiple dependencies) can be claimed as well, so that any combination of claims and the features thereof are disclosed and can be claimed regardless of the dependencies chosen in the attached claims. The subject-matter which can be claimed includes not only the combinations of features as set out in the attached claims but also any other combination of features in the claims, wherein each feature mentioned in the claims can be combined with any other feature or combination of other features in the claims. Furthermore, any one of the embodiments and features described or depicted herein can be claimed in a separate claim and/or in any combination with any embodiment or feature described or depicted herein or with any one of the features of the attached claims.

BRIEF DESCRIPTION OF THE DRAWINGS

FIG. 8 illustrates an example model performance lookup table.

FIG. 13 illustrates example results for different metrics before and after applying an improved method of outlier detection and removal discussed herein.

FIG. 14 illustrates example thresholds determined for different metrics for outlier removal and amount of data loss compared to standard z-score technique in outlier removal using the thresholds determined for these metrics.

FIG. 16 illustrates an example method of using model routing to predict a plurality of metrics for a clinical study.

FIG. 17 illustrates an example method for determining an adaptive threshold for outlier detection and removal.

FIG. 18 illustrates an example method for outlier detection and removal using an adaptive threshold.

DESCRIPTION OF EXAMPLE EMBODIMENTS

Model Routing

Figure 1:
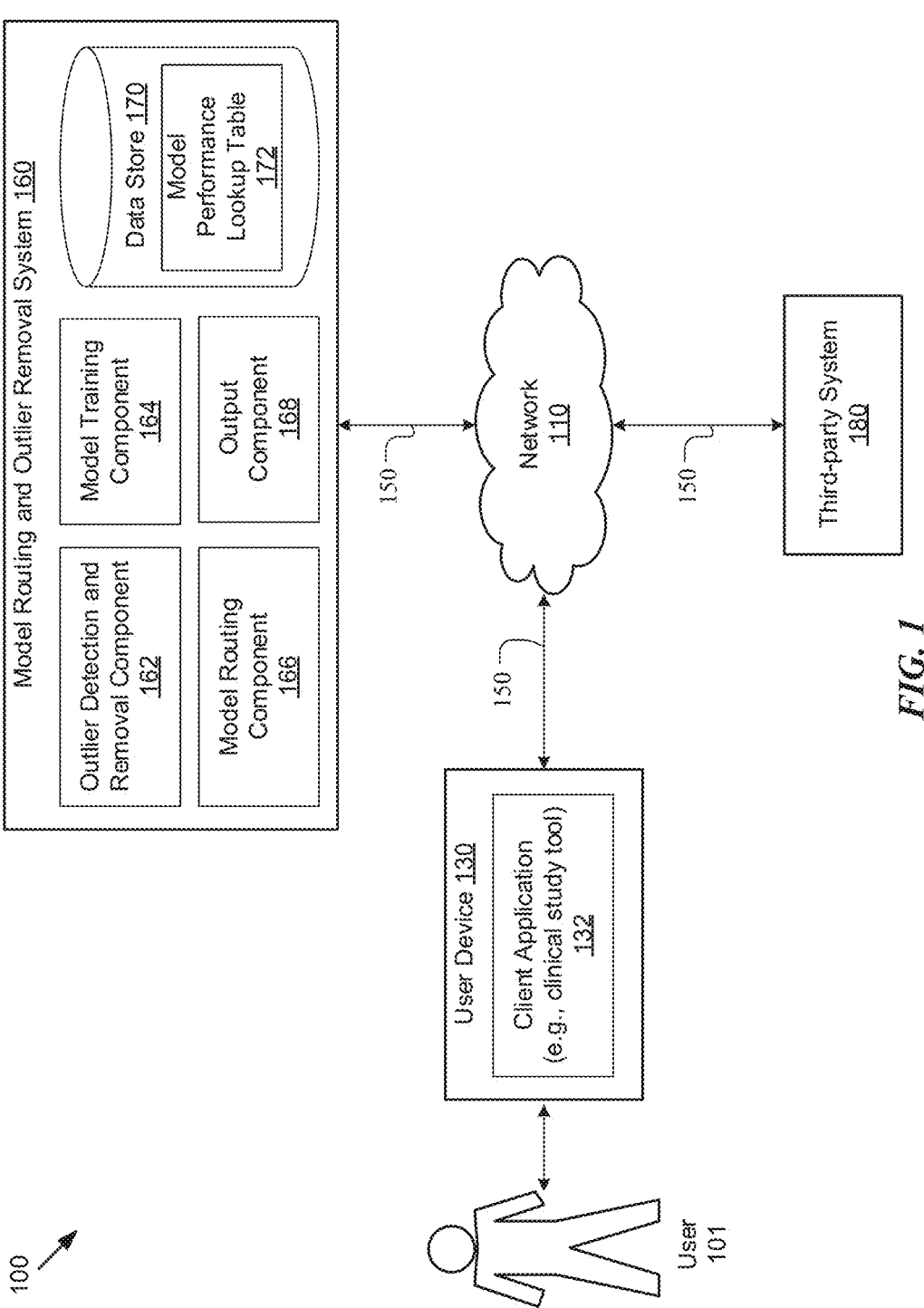
FIG. 1 illustrates an example network environment associated with a model routing and outlier removal system.

A user (e.g., a clinical scientist) may design various protocols or studies that describe patient data associated with a set of clinical-study metrics, such as enrollment rate of patients per month, screening rate of patients per month, a screen failure ratio, a patient dropout ratio, etc. These studies or protocols may be designed for various categories associated with a clinical study or trial, such as for different phases of the clinical trial (e.g., phase 1 study, phase 2 study, etc.) and for different therapeutic areas (e.g., oncology, neurology, ophthalmology, dermatology, etc.). A machine learning (ML) model may be trained to predict the set of clinical-study metrics. However, using a single trained model (e.g., a baseline model) to predict the metrics for all the categories may be prone to errors and sometimes result in inaccurate predictions especially when the model is used on a dataset that has multiple overlapping categories of data. Accuracy in predictions may be improved if multiple fine-grained ML models are trained for the different categories, such that there is a separate ML model for each category (e.g., a phase 1 model, a phase 2 model, an oncology model, etc.). However, with all these different trained ML models, it is a challenge to decide at inference or run time which model to choose for predicting a metric that provides the most accurate prediction among the different models.

Particular embodiments describe multiple fine-grained machine-learning models for different categories of a dataset, instead of one generic model, and efficiently selecting a correct fine-grained model at inference time to make a prediction on a new input or a clinical study. This efficient selection of a model (also herein referred to as model routing) may be broadly useful whenever a machine learning model is used on a dataset that has multiple overlapping categories of data. For example, model routing may be used in a clinical study tool, which is a tool used for evaluating or assessing protocols, clinical studies, or clinical trials. In some embodiments, the clinical study tool may a machine-learning model trained on operational data from clinical studies, and used by users (e.g., clinical scientists) for predicting multiple operational metrics for a clinical study or trial based on protocol eligibility criteria text and study metadata, as shown for example in FIG. 4. Example graphical user interfaces associated with the clinical study tool are shown in FIGS. 15A-15H.

In particular embodiments, model routing implementation may include that rather than using a same model or baseline model for studies of all different categories, such as all phases and therapeutic areas (TAs), using different models trained on specific categories. For instance, there may be a model trained on specific phase category, a model trained on specific TA category, etc. To train the different models, a training dataset is filtered or sliced by each category, for example, by phase or by TA, and then a category-specific model is separately trained for each phase and for each TA. Also, a generic or a baseline model is trained based on the whole training dataset without filtering. Then performance of these trained models, including the baseline model and the different category-specific models, during testing are stored in a model performance lookup table. In some embodiments, the machine-learning models discussed herein are supervised machine-learning models, and could be regression, classification, or tree-based models. In some embodiments, these models may be trained on structured/tabular data (as opposed to unstructured data). Non-limiting examples of tree-based models may include random forest, XGBoost, or LightGBM.

In particular embodiments, model routing i.e., selecting an appropriate model from the trained machine-learning models, including the baseline model and the different category-specific models, may be used in a clinical-study tool for making various predictions on a new clinical study. For example, as shown in FIG. 15D or 15F, given user inputs, such as selection of a therapeutic area, a study phase, a clinical-study metric, etc., a model routing algorithm may select an appropriate trained model for predicting values for that clinical-study metric. As shown in FIG. 15D, the selected model by the model routing algorithm may output a prediction for an enrollment rate (e.g., patients/month)

metric. Similarly, different models may be selected for predicting other clinical-study metrics, such as screening rate of patients, a screen failure ratio, a patient dropout ratio, etc. Using the predicted values by the models for the clinical-study metrics, predictions or data driven insights, such as operational burden measures, site burden measures, patient burden measures, etc. may be generated for display on a graphical user interface of the clinical-study tool, as shown in FIG. 15H. Users (e.g., clinical scientists) may use these predictions during a protocol designing phase to design patient and investigator centric protocols, as shown and discussed in reference to FIG. 4.

Although the model routing is discussed herein with respect to two categories phase and TA, it should be noted that this is not limiting and additional categories are also possible and within the scope of the present disclosure. For instance, the model routing can be easily extended to additional categories (e.g., indications, disease areas (more specific than therapeutic areas), molecules, etc.) without sacrificing the size of the dataset to train the models, and therefore the model quality.

FIG. 1 illustrates an example network environment 100 associated with a model routing and outlier removal system. Network environment 100 includes a user 101, a user device 130 including a client application 132 (e.g., clinical study tool), a model routing and outlier removal system 160, and a third-party system 180 connected to each other by a network 110. Although FIG. 1 illustrates a particular arrangement of user 101, user device 130, a model routing and outlier removal system 160, third-party system 180, and network 110, this disclosure contemplates any suitable arrangement of user 101, user device 130, a model routing and outlier removal system 160, third-party system 180, and network 110. As an example and not by way of limitation, two or more of user device 130, model routing and outlier removal system 160, and third-party system 180 may be connected to each other directly, bypassing network 110. As another example, two or more of client system 130, model routing and outlier removal system 160, and third-party system 180 may be physically or logically co-located with each other in whole or in part. Moreover, although FIG. 1 illustrates a particular number of users 101, user devices 130, model routing and outlier removal systems 160, third-party systems 170, and networks 110, this disclosure contemplates any suitable number of users 101, user devices 130, model routing and outlier removal systems 160, third-party systems 170, and networks 110. As an example and not by way of limitation, network environment 100 may include multiple users 101, user devices 130, model routing and outlier removal systems 160, third-party systems 170, and networks 110.

In particular embodiments, user 101 may be an individual (human user) such as a clinical scientist that interacts or communicates with or over model routing and outlier removal system 160. In particular embodiments, the model routing and outlier removal system 160 may be a network-addressable computing system for (1) predicting a plurality of clinical-study metrics for a clinical study using one or more machine learning models (e.g., baseline model, category-specific models) through model routing and (2) removing outliers from a training dataset using an adaptive threshold and a particular scoring technique (e.g., a modified z-score technique). As depicted, the model routing and outlier removal system 160 includes an outlier detection and removal component 162, a model training component 164, a model routing component 166, an output component 168, and a data store 170. It should be noted that the model routing and outlier removal system 160 is not limited to these components 162-170 and additional components are also possible and within the scope of the present disclosure. For example, there may be a component for performing validation of model routing, as discussed in reference to FIGS. 9 and 10. There may be a component for deploying the trained models i.e., deployment inference pipeline, as discussed in reference to FIG. 2. There may be a component for preprocessing the data overall (e.g., filtering out invalid studies), which may occur before the outlier detection and removal process discussed herein. There may be a component for preprocessing the dataset on a per-metric basis (e.g., imputing certain missing values, removing rows with null values in the target, dropping columns with more than a certain number of missing values, e.g., 80% dropping correlated features, replacing rare categories with "other", etc.). It should be noted that the preprocessing step for the overall data may occur before the outlier detection and removal process discussed herein, whereas the per-metric preprocessing step may occur after the outlier detection and removal process.

The outlier detection and removal component 162 may be configured to remove outliers from a training dataset using an improved method for data-loss-conscious outlier detection and removal discussed herein. To remove the outliers, the outlier detection and removal component 162 may first determine an adaptive threshold using an iterative process (e.g., as shown and discussed in FIG. 17) and then use the adaptive threshold and a particular scoring technique (e.g., a modified z-score technique) to detect and remove the outliers from the data (e.g., as shown and discussed in FIG. 18). Detailed description regarding outlier detection and removal is provided below in reference to at least FIGS. 11-14, 17, and 18.

The model training component 164 may be configured to train a baseline model and a plurality of category-specific machine-learning (ML) models. The model training component 164 may receive or access a training dataset resulting after the outlier removal by the outlier detection and removal component 162. The training dataset may include ground-truth values for multiple categories. The model training component 164 may train the baseline model based on the whole dataset. For training the plurality of category-specific ML models, the model training component 164 first filters the dataset by each category so that for each category, there is a category-specific training dataset. For example, after filtering, there may be a first training dataset for phase 1 category, a second training dataset for phase 2 category, a third training dataset for TA oncology (ONC) category, a fourth training dataset for TA neuroscience (NS) category, and so on. The model training component 164 may use each category-specific training dataset to build or train a corresponding category-specific ML model resulting in, for example, a phase 1 model, a phase 2 model, a TA ONC model, a TA NS model, etc. Detailed description regarding training the baseline and category-specific ML models is covered below in reference to at least FIG. 6.

The model training component 164 may further be configured to prepare a model performance lookup table 172. For instance, after the models are sufficiently trained, the model training component 164 may test each of the models, including the baseline model and category-specific ML models to predict values for a plurality of clinical-study metrics (e.g., enrollment rate of patients, screen failure ratio, patient dropout ratio, screening rate of patients, time to first patient, etc.). In some embodiments, the testing may be done using cross-validation with multiple folds of test sets (e.g., whose data points are not seen at training time). The performance (e.g., RMSE) may be measured for each of the test folds and the average may be reported across these folds. In some embodiments, the performance of each model may be recorded in an experiment tracking system (e.g., hosted on a separate server and accessed via API calls). Results may be downloaded or retrieved from the experiment tracking system and then for each of the category-specific ML models, a difference in performance between that category-specific ML model and the baseline model is measured. In particular embodiments, this measure of difference in performance between the category-specific ML model and the baseline model is measured by taking the difference in RMSE between the two models, dividing by the RMSE for the baseline model, and multiplying by 100 to get a percentage difference, as discussed elsewhere herein. Measurement values indicating performance of each category-specific ML model (e.g., percent difference in RMSE from baseline) is then stored in cells of the table 172, where each column of the table 172 corresponds to measurement values for one of the category-specific ML models within a particular category, as shown for example in FIG. 8. In particular embodiments, the model training component 164 may store the model performance lookup table in the data store 170 for later access and/or retrieval. Detailed description regarding the model performance lookup table is covered below in reference to at least FIGS. 6 and 8.

It should be noted that the present disclosure is not limited to measuring performance of models through RMSE and other measuring criteria are also possible and within the scope of the present disclosure. RMSE is merely one example of performance measure that could be used for a regression model, but one could instead choose to use a classification model, in which case accuracy, precision, recall, or F1 score are instead used to measure performance. The clinical study tool discussed herein may work the same whether one uses a regression model or the classification model. The important thing to consider is that when predicting the plurality of clinical-study metrics, the model used should be consistent i.e., the plurality of metrics should all be predicted by a classification model, or all be predicted by a regression model, but not a mix of both.

Also, it should be noted that the present disclosure is not limited to selecting models based on percent difference in RMSE between a category-specific model and the baseline model and other ways of selecting models are also possible and contemplated. For example, it is also possible to combine this with other measures of performance (e.g., percentage of perturbation tests passes) into an aggregate score and use this to select between models instead. Each measure of performance would either need to be assigned a weight based on importance, or ranked (e.g., first check if the percent difference from baseline<−10%, then check if over 80% of perturbation tests pass then check if RMSE<Q1 of the target value.

Figure 3:
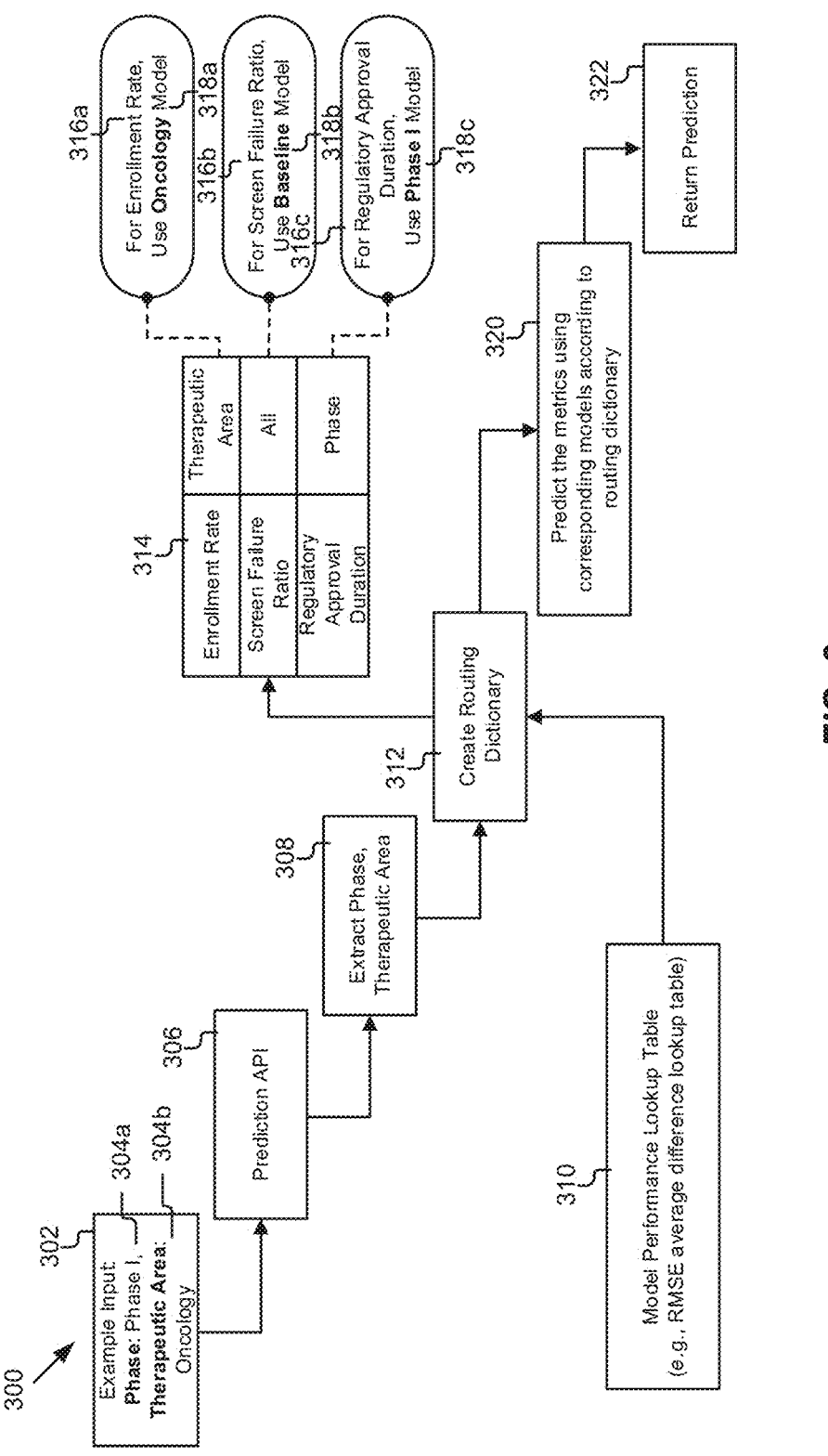
FIG. 3 illustrates an example model routing at inference time.

The model routing component 166 (also interchangeably referred to as model routing algorithm) may be used to select appropriate models for making a prediction on a new clinical study (e.g., as shown in FIG. 3). For making the prediction on the new clinical study, a user input is received. For instance, a subcategory for each category is received from the user about which the user wants to make a prediction. By way of an example, the user wants to make a prediction where the phase subcategory is 1, and the TA subcategory is ONC. Then based on the user received or selected subcategories, the model routing component 166 may compare performances of category-specific ML models corresponding to these selected subcategories with respect to the baseline model using the model performance lookup table 172. If they are all worse than the baseline model, then the model routing component 166 selects the baseline model. Otherwise, the model routing component 166 selects a category-specific ML model with the best performance according to the model performance lookup table 172. Based on the selections, the model routing component 166 may create a routing dictionary. The routing dictionary may include a selected model for each of a plurality of metrics for prediction. An example routing dictionary 314 is shown in FIG. 3.

Figure 4:
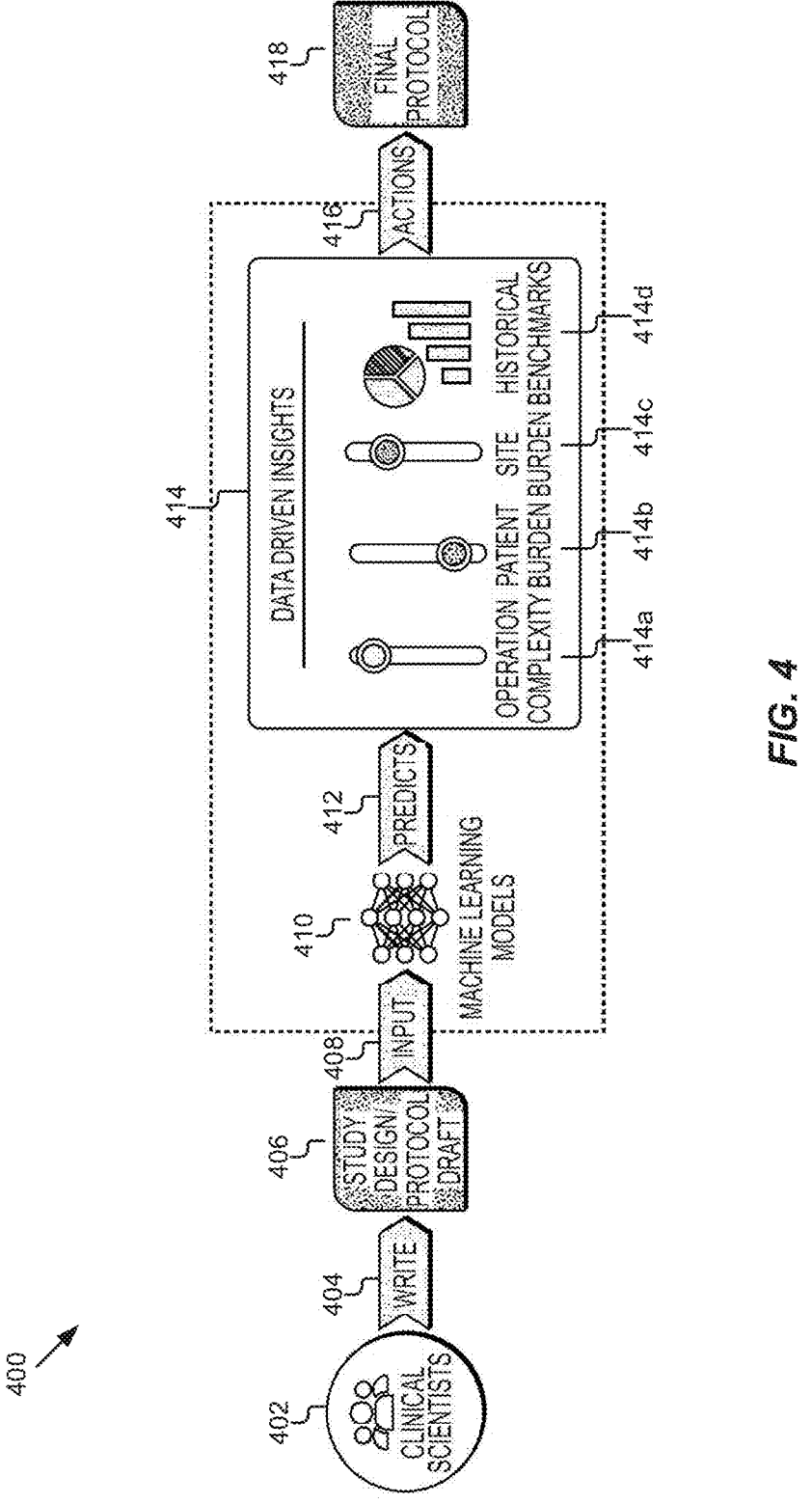
FIG. 4 illustrates an example use of machine-learning models and their predictions during a protocol design phase.

The output component 168 may be configured to predict a plurality of metrics (e.g., enrollment rate, screening rate, etc.) according to the routing dictionary prepared by the model routing component 166. For instance, the output component 168 may predict values for the plurality of metrics using corresponding selected models in the routing dictionary. The output component 168 may also be configured to generate an output for the clinical study based on the predicted values for the plurality of metrics. In particular embodiments, the output for the clinical study may include data driven insights including an operational complexity or operational burden measures, patient burden measures, site burden measures, and historical benchmarks, as shown in FIG. 4 or FIG. 15H. In particular embodiments, the output component 168 may provide these data driven insights or predictions for different metrics for display on a graphical user interface of the client application 132 (e.g., clinical study tool). Example outputs are shown in FIGS. 15D, 15F, and 15H. A user 101 (e.g., clinical scientist) may use these outputs (e.g., data driven insights or predictions) during the protocol design phase to design patient and investigator centric protocols.

The model routing and outlier removal system 160 may be accessed by the other components of network environment 100 either directly or via network 110. Third-party system 180 may be accessed by the other components of network environment 100 either directly or via network 110. In particular embodiments, one or more users 101 may use one or more user devices 130 to access, send data to, and receive data from the model routing and outlier removal system 160 or third-party system 180. User device 130 may access the model routing and outlier removal system 160 or third-party system 180 directly, via network 110, or via a third-party system. As an example and not by way of limitation, user device 130 may access third-party system 180 via the model routing and outlier removal system 160. User device 130 may be any suitable computing device, such as, for example, a personal computer, a laptop computer, a cellular telephone, a smartphone, a tablet computer, or an augmented/virtual reality device.

This disclosure contemplates any suitable network 110. As an example and not by way of limitation, one or more portions of network 110 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or a combination of two or more of these. Network 110 may include one or more networks 110.

Links 150 may connect user device 130, model routing and outlier removal system 160, and third-party system 180 to communication network 110 or to each other. This disclosure contemplates any suitable links 150. In particular embodiments, one or more links 150 include one or more wireline (such as for example Digital Subscriber Line (DSL) or Data Over Cable Service Interface Specification (DOC-SIS)), wireless (such as for example Wi-Fi or Worldwide Interoperability for Microwave Access (WiMAX)), or optical (such as for example Synchronous Optical Network (SONET) or Synchronous Digital Hierarchy (SDH)) links. In particular embodiments, one or more links 150 each include an ad hoc network, an intranet, an extranet, a VPN, a LAN, a WLAN, a WAN, a WWAN, a MAN, a portion of the Internet, a portion of the PSTN, a cellular technology-based network, a satellite communications technology-based network, another link 150, or a combination of two or more such links 150. Links 150 need not necessarily be the same throughout network environment 100. One or more first links 150 may differ in one or more respects from one or more second links 150.

Figure 2:
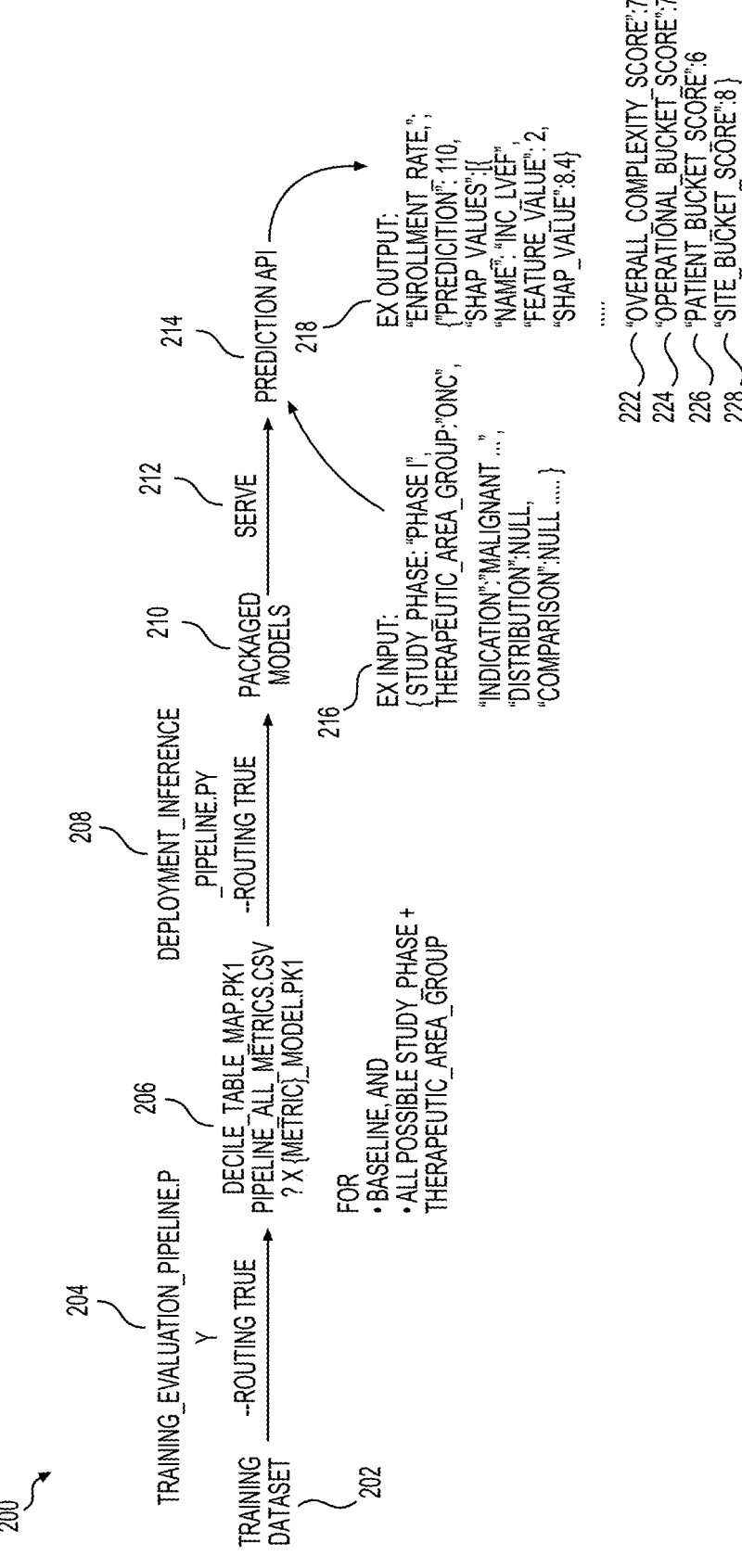
FIG. 2 illustrates an example overview of a model routing pipeline.

FIG. 2 illustrates an example overview of a model routing pipeline 200. In particular, the model routing pipeline 200 shows high-level steps that are involved during training and deployment of the various models, including baseline and category-specific ML models, into production so that these models can be utilized by the model routing algorithm at inference time for making a prediction on new user data or clinical study, as shown for example in FIG. 3. The model routing pipeline 200 starts with receiving a training dataset at step 202. The training dataset may include ground-truth or true values for a plurality of clinical-study metrics (e.g., enrollment rate of patients, screen failure ratio, patient dropout ratio, screening rate of patients, time to first patient, etc.) associated with multiple categories, such as phase and TA categories. In particular embodiments, the training dataset is obtained in a comma-separated values (csv) file format, where ground-truth or true values for the metrics are separated by commas. The training dataset is filtered by each subcategory of the multiple categories to obtain a plurality of category-specific training datasets (e.g., a phase 1 category dataset, a phase 2 category dataset, an ONC category dataset, etc.).

At step 204, the entire training dataset (e.g., without filtering) and category-specific training datasets (e.g., obtained after filtering) goes through a training evaluation pipeline to train and build the baseline model and category-specific ML models. Detailed description regarding the training is covered below in reference to FIG. 6.

At step 206, based on the training, a baseline model and a plurality of category-specific ML models are obtained. In particular embodiments, each of the models is formatted into a particular file format, such as a serialized pickle file (.pkl file). A pkl file is a file created by pickle, a Python module that enables objects to be serialized to files on disk and de-serialized back into the program at runtime. Each file associated with a model may include parameters and configurations of that model for each metric of the plurality of clinical-study metrics. For instance, for the 9 clinical-study metrics, as shown in FIG. 8, there may be a file for each metric for a model or in other words there will be 9 baseline models for the 9 clinical-study metrics. Similarly, there may be 9 or fewer phase 1 models for the 9 metrics, 9 or fewer phase 2 models for the 9 metrics, 9 or fewer TA ONC models for the 9 metrics, etc. The reason that there may not be all 9 category-specific model (e.g., phase 1 models) for the 9 metrics is because the performance of that category-specific model may suboptimal or worse than the baseline model for a particular metric, and therefore there is no need to store that model or create a separate file for that model. By way of a non-limiting example, a first file associated with a baseline model may include parameters and configurations for a first clinical-study metric (e.g., enrollment rate), a second file associated with the baseline model may include parameters and configurations for a second clinical-study metric (e.g., screening rate), a file associated with a TA ONC model may include parameters and configurations for the first clinical-study metric, etc. By way of another non-limiting example, a file associated with a phase 1 model may include parameters and configurations for a particular clinical-study metric for the phase 1 category of patients. Similarly, a file associated with a TA ONC model may include predicted values for the 9 metrics for the patients categorized under oncology therapeutic area.

At step 208, the baseline model and the plurality of category-specific ML models goes through a deployment inference pipeline to deploy these models into production. The deployment may incorporate a logic to choose which models to use at inference time or run time upon receiving an input from the user. Then at step 210, the baseline model and the plurality of category-specific ML models are packaged into a container or framework for serving, managing, and deploying the various machine learning models. In particular embodiments, the trained baseline model and the plurality of category-specific ML models are packaged into a BentoML framework, which is then served (step 212) into a prediction application programming interface (API) 214. When a new user input 216 for a particular clinical study is received at run time, the prediction API 214 may be called to generate an output 218 for the particular clinical study including predicted values for the various metrics, such as enrollment rate 220, and overall complexity score 222, operational bucket score 224, patient bucket score 226, and site bucket score 228 based on the predicted values for the various metrics. The overall complexity score 222 is a combination of operational complexity (e.g., reflected by operational bucket score 224), patient burden (e.g., reflected by patient burden score 226), and site burden (e.g., site burden score 228) and is used to reflect the overall complexity of a clinical study or trial. The various predictions made based on the plurality of clinical-study metrics are further discussed in detail below in reference to FIG. 15H.

FIG. 3 illustrates an example model routing 300 at inference time. In particular embodiments, the model routing 300 is performed by a model routing algorithm. At step 302, the model routing algorithm receives an example user input. The user input may include one or more user selected subcategories from one or more categories associated with a clinical study for which the user wants a prediction based on a plurality of metrics. For example, as shown, the user input specifies a phase 1 subcategory 304a and ONC subcategory 304b from the phase and TA categories. After receiving the user input, at step 306, the model routing algorithm makes a call to a prediction API (e.g., prediction API 214) to access or retrieve the various models and the model performance lookup table. As discussed elsewhere herein, the model performance lookup table includes performance benchmarks of the category-specific ML models with respect to the baseline model in predicting the plurality of metrics. The performance benchmarks may be listed in the form of percentage difference in RMSE from baseline RMSE for each category-specific model.

At step 308, the model routing algorithm may extract the user-selected subcategories from the model performance lookup table and compare the performance of the baseline model and category-specific ML models corresponding to the user selected sub-categories. For instance, the model routing algorithm may extract the phase 1 and ONC columns from the table 310 and compare the percent differences in RMSE from the baseline RMSE of the category-specific ML models in the two columns. A detailed model performance lookup table is shown in FIG. 8. As shown in FIG. 8, the percent differences (e.g., also herein interchangeably referred to as values) in the table indicates a reduction in error or in other words better accuracy when predicting a particular metric by the category-specific ML model as compared to the baseline model. Lower the percent difference or value (e.g., greater the negative value), greater the accuracy of a particular category-specific ML model. Here "X" in the table indicates that there was no significant improvement, or the improvement was less than a certain threshold (e.g., 10%) when using a category-specific model as compared to the baseline model for predicting a particular clinical-study metric. Stated differently, X may indicate that the accuracy of the baseline model was found better than the category-specific ML model for a particular metric.

Based on comparing the percent differences in RMSE between the category-specific model(s) and the baseline model in the table 310, at step 312, the model routing algorithm may create a routing dictionary 314. The routing dictionary 314 may highlight or indicate a model that is selected by the model routing algorithm for predicting a metric based on the performance benchmarks (e.g., RMSE percentage differences) in the model performance lookup table 310. As depicted, for predicting the enrollment rate metric 316a, the model routing algorithm selects the ONC model 318a; for predicting the screen fail ratio metric 316b, the model routing algorithm selects the baseline model 318b; and for predicting the regulatory approval duration (e.g., time from internal protocol approval (FPA) to first regulatory approval (FRA)) metric 316c, the model routing algorithm selects the phase 1 model 318c.

At step 320, the model routing algorithm may predict values for the plurality of clinical-study metrics (e.g., the 9 metrics as shown in FIG. 8) using corresponding selected models according to the routing dictionary 314. At step 322, the model routing algorithm may return or output a prediction for the requested clinical study based on the values for the plurality of clinical-study metrics. The prediction may include, for example and without limitation, operational burden measures, patient burden measures, site burden measures, etc. An example prediction for a clinical study is shown in FIG. 15H.

FIG. 4 illustrates an example use of machine-learning models discussed herein and their predictions during a protocol design phase 400. The predictions help clinical scientists 402 make informed decisions while they are in the protocol design phase 400 to design patient and investigator centric protocols. The protocol design phase 400 starts with the clinical scientists 402 writing 404 an initial protocol draft 406 that may include, for example and without limitation, inclusion/exclusion criteria, eligibility criteria, features from schedule of assessment table, etc. In some embodiments, inclusion and exclusion criteria are two types of eligibility criteria. The eligibility criteria may describe characteristics that define whether patients be included in a clinical study or excluded from the clinical study. A schedule of assessment table may contain a list of assessments and/or procedures that a patient may undergo during a study. The initial protocol draft 406 is provided as input 408 to the various machine learning models 410, including the baseline model and a plurality of category-specific ML models discussed herein. The model routing algorithm may use or select appropriate models from these machine learning models 410, based on the technique discussed above in reference to FIG. 3, and predicts 412 a plurality of data driven insights

414. These data driven insights 414 may include, for example, an operational complexity 414a, a patient burden 414b, a site burden 414c, and historical benchmarks 414d. The operational complexity 414a may indicate the complexity faced by a team running a clinical study. The patient burden 414b may indicate the burden faced by a patient who is participating in the study. The site burden 414c may indicate the burden faced by clinical site(s) at which the study takes place. The historical benchmarks 414d may represent past studies and their associated data. The past studies may be provided so that users can compare their prospective study to these studies with similar characteristics, and benchmark(s) against the performance of these studies in various operational measures captured by the plurality of clinical-study metrics discussed herein. In particular embodiments, these data driven insights 414 may be output on a graphical user interface of a clinical study tool, such as the graphical user interface shown in FIG. 15H. The clinical scientists 402 may use these data driven insights 414 to perform one or more actions 416, such as designing their final protocol 418.

Figure 5:
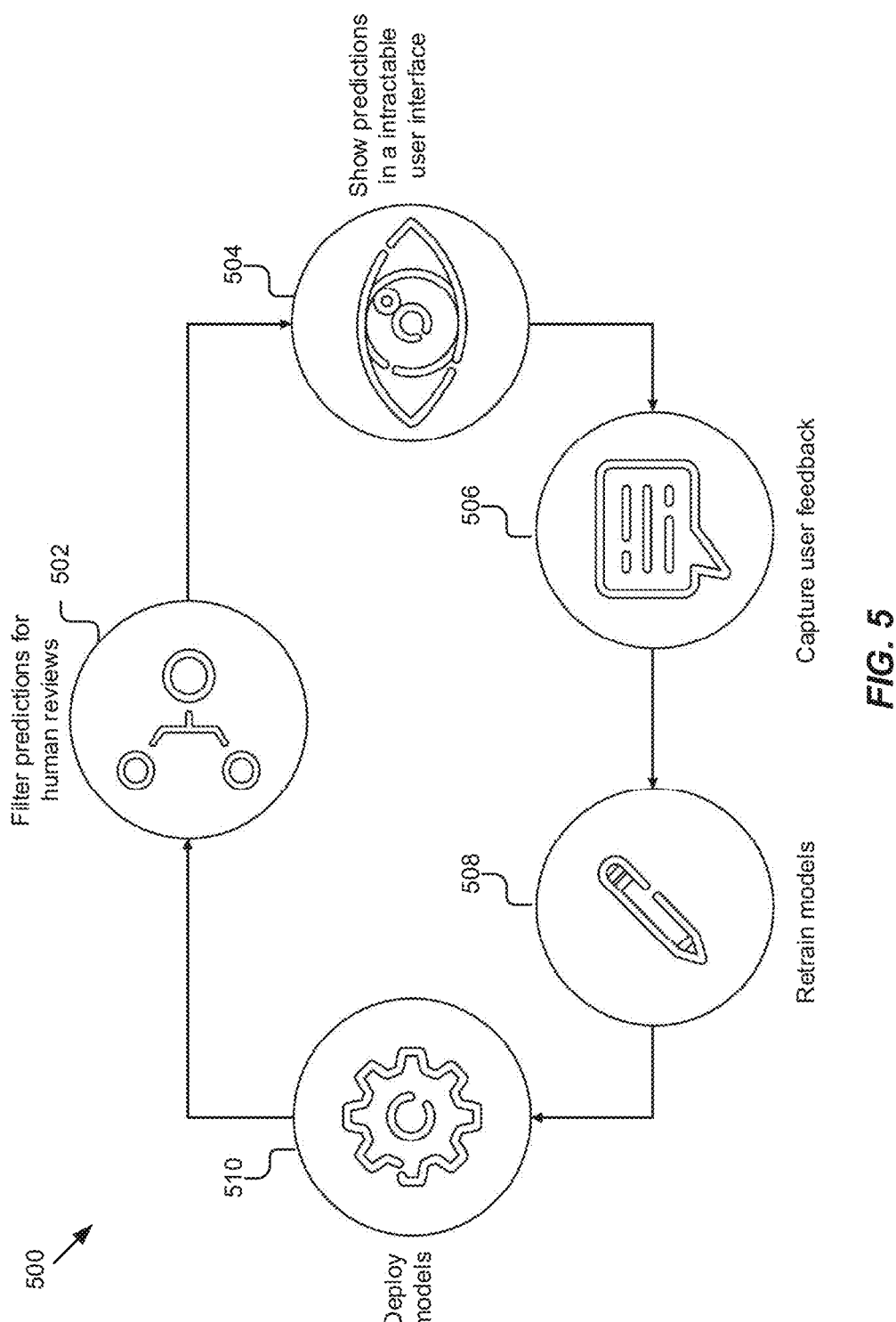
FIG. 5 illustrates an example human validation lifecycle for validating results of predictions by the machine learning models and re-training of the models based on user feedback.

FIG. 5 illustrates an example human validation lifecycle 500 for validating results of predictions by the machine learning models and re-training of the models based on user feedback. The human validation cycle 500 starts, at step 502, by filtering predictions for human reviews. In particular embodiments, filtering the predictions may include separating the predictions into high-confidence predictions and low-confidence predictions. These high-confidence predictions and low-confidence predictions may be filtered out based on confidence scores associated with these predictions. For instance, the predictions that are made by the various machine-learning models, as discussed above in reference to FIGS. 3-4, may be assigned confidence scores. Predictions for clinical-study metrics (e.g., enrollment rate, screening rate, screen failure ratio, etc.) whose predicted values by the ML models are close to the true values may be assigned high confidence scores, whereas predictions for metrics whose predicted values by the ML models are significantly far away from the true values may be assigned low confidence scores. In some embodiments, the ground-truth values may be known for certain data points and unknown for other data points. For example, predictions that are made on new data, ground-truth values may not be known at inference time and estimated confidence scores may be determined for these predictions for new data with unknown ground-truth values. In particular embodiments, the high-confidence predictions (e.g., predictions with high confidence scores) may be immediately returned to a client application, such as a clinical study tool discussed herein. At step 504, low-confidence predictions (e.g., predictions with low confidence scores) may be shown to a user (e.g., a clinical scientist) in an intractable user interface. At 506, the user may provide their feedback on these low-confidence predictions. At step 508, the user feedback may be used to retrain one or more models (e.g., category-specific ML models) that are associated with these low-confidence predictions. At step 510, once the one or more models are retrained, these retrained models are again deployed for production (e.g., using the deployment pipeline discussed above in reference to FIG. 2) so that they can be used to make predictions at run time. Again, a subsequent set of predictions may be evaluated, and steps 502-510 may be repeated until the models are sufficiently trained or reach to the point that they completely or mostly generate high-confidence predictions.

Figure 6:
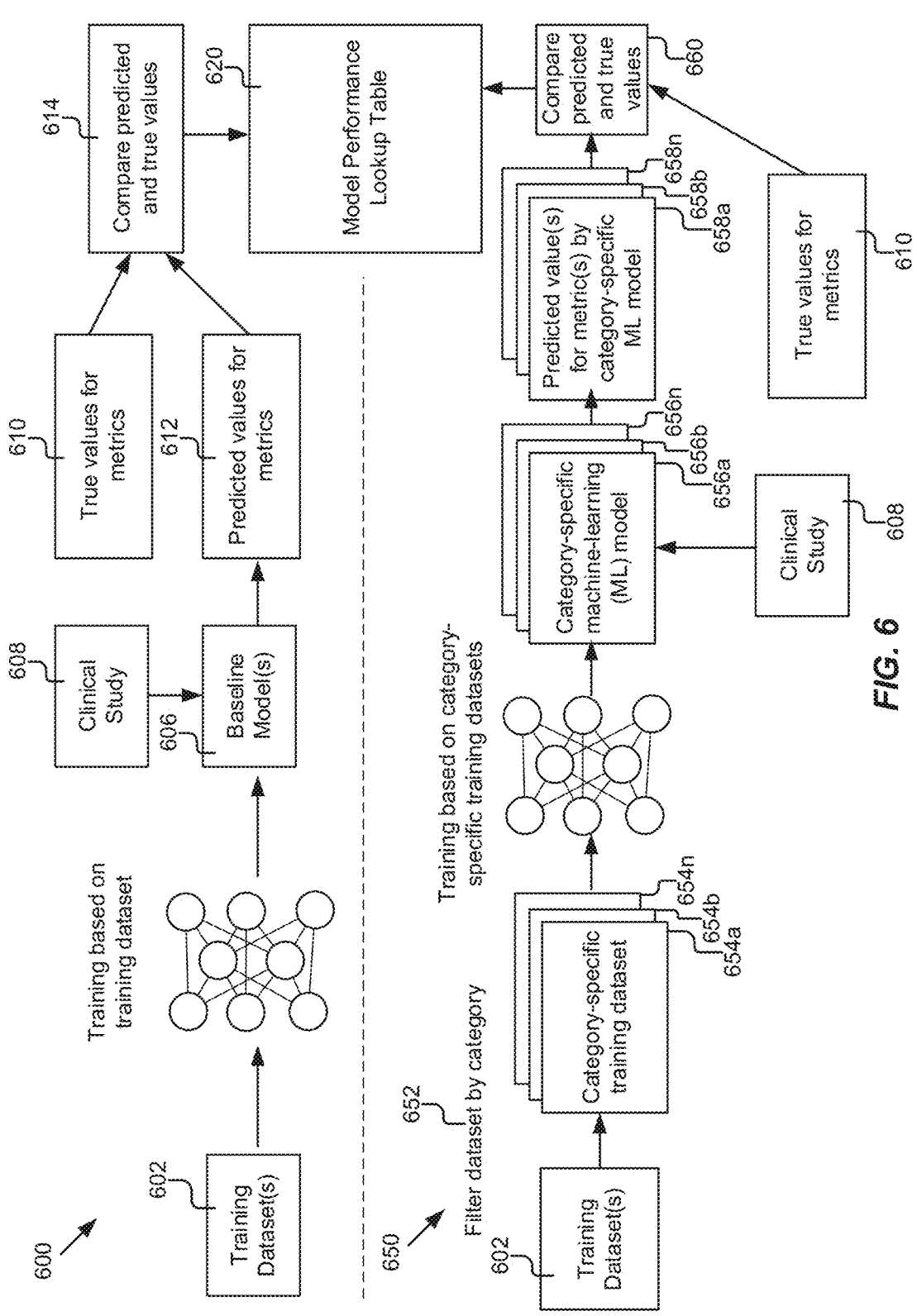
FIG. 6 illustrates example methods for training a baseline model and a plurality of category-specific ML models, respectively.

FIG. 6 illustrates example methods 600 and 650 for training a baseline model and a plurality of category-specific ML models, respectively. The method 600 for training the baseline model begins by receiving or assessing a training dataset 602. The training dataset 602 may include ground-truth or true values for a plurality of clinical-study metrics associated with multiple categories (e.g., phase, TA). In some embodiments, prior to training the models using the training dataset 602, one or more preprocessing steps may be applied on the training dataset 602 so as to optimize the training and improve the accuracy of a model's predictions when trained on this dataset 602.

Figure 7:
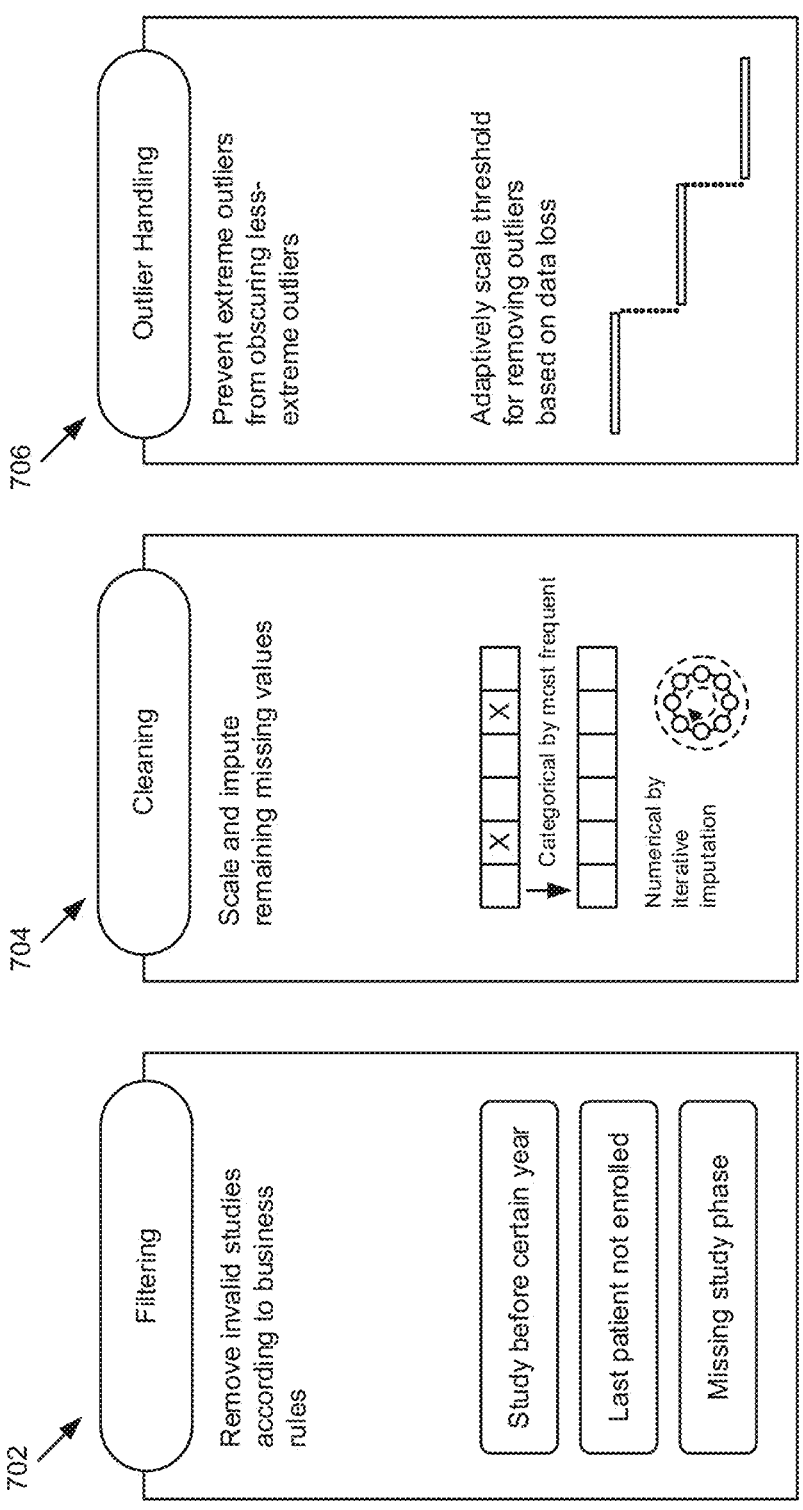
FIG. 7 illustrates example pre-processing steps that may be applied on a training dataset for training machine learning models.

FIG. 7 illustrates example pre-processing steps that may be applied on the training dataset 602 for training the machine learning models. These pre-processing steps may include a filtering step 702, a cleaning step 704, and outlier handling step 706. In the filtering step 702, invalid clinical studies are removed from the training dataset 602 according to some rules, such as business rules. Some of these rules may include, for example and without limitation, studies before a particular year (e.g., studies prior to year 2009), studies without a last patient enrolled, studies with a missing phase, etc. In the cleaning step 704, missing values in the remaining study records may be scaled and imputed. Imputation may be done for categorical features based on most frequent observation, and for numerical features using round-robin linear regression. In the outlier handing step 706, an adaptive threshold is determined and used for removing outliers from the training dataset 602 to avoid excessive loss of data and to prevent extreme outliers from obscuring less-extreme outliers. Detailed description regarding the outlier handing step 706 is covered below in reference to at least FIGS. 11-14, 17, and 18.

Returning to FIG. 6, once the training dataset 602 is pre-processed using the one or more pre-processing steps 702-706 of FIG. 7, a model may be trained based on the entire training dataset 602 to generate a baseline model 606. In particular embodiments, there may be a training dataset 602 associated with each metric of the plurality of clinical-study metrics discussed herein and a baseline model 606 is generated for each metric based on the training dataset 602 corresponding to that metric. By way of an example, if there are 9 clinical-study metrics, they may be 9 training datasets corresponding to these metrics, and the training may be performed based on these 9 training datasets to generate 9 baseline models. Then the trained one or more baseline models 606 may be tested to determine their accuracy in predicting values for one or more clinical-study metrics (e.g., enrollment rate, screening rate, screen failure ratio, etc.) for a particular clinical study 608 whose true values 610 for the metrics are known. In particular embodiments, testing the one or more baseline models 606 may include receiving input for the particular clinical study 608 and using the one or more baseline models 606 to generate predicted values 612 for the one or more clinical-study metrics. Then predicted values 612 and the true values 610 for the metrics are compared 614 to determine an accuracy or confidence in the prediction of metrics by the one or more baseline models. If the accuracy or confidence in predictions is greater than a certain threshold (e.g., above a certain confidence score), then the one or more baseline models 606 may be determined to be sufficiently trained and ready for deployment. Otherwise, the one or more baseline models 606 are re-evaluated qualitatively, their features are re-engineered, and their training data quality further investigated and improved until the accuracy or confidence in their predictions meets threshold criteria.

In particular embodiments, every time the one or more baseline models are tested, results of testing are stored in a data store for future access and/or retrieval or in the form of a lookup table, such as a model performance lookup table 620, which is used at inference or run time by the model routing algorithm to select an appropriate model for a metric, as discussed elsewhere herein. In some implementations, based on the comparison 614 of the predicted and true values, performance benchmarks of the one or more baseline models 606 may be stored in the model performance lookup table 620 in the form of RMSE percent differences compared to category-specific models. In some embodiments, the performance benchmarks may include a particular measure or indicator of the difference in the predicted values 612 by the baseline model 606 and the true values 610.

The method 650 for training the category-specific ML models is somewhat similar but instead of training these models based on the entire training dataset 602 like the baseline model 606, different models are trained on datasets filtered by categories or in other words a specific model for each category is trained based on dataset corresponding to that category. The method 650 begins by receiving or assessing the training dataset 602 and then filtering 652 the dataset 602 by one or more categories of phase and TA to generate category-specific datasets 654a, 654b, . . . , 654n (also individually and collectively referred to herein as 654). For example, category-specific training dataset 654a contains ground-truth/true values for clinical-study metrics associated with phase 1 category, category-specific training dataset 654b contains ground-truth/true values for clinical-study metrics associated with phase 2 category, and category-specific training dataset 654n contains ground-truth/true values for clinical-study metrics associated with TA ONC category, etc. Then different models are trained based on these category-specific datasets 654a, 654b, . . . , 654n to generate corresponding category-specific ML models 656a, 656b, . . . , 656n (also individually and collectively referred to herein as 656). For example, the category-specific training dataset 654a associated with the phase 1 category is used to generate a corresponding phase 1 model 656a configured to predict metrics for studies (or in other words clinical-study metrics) in the phase 1 category, the category-specific training dataset 654b associated with the phase 2 category is used to generate a corresponding phase 2 model 656b configured to predict metrics for studies in the phase 2 category, and the category-specific training dataset 654n associated with the TA ONC category is used to generate a corresponding TA ONC model 656n configured to predict metrics for studies in the TA ONC category.

Then similar to the one or more baseline models 606, the category-specific ML models 656a, 656b, . . . , 656n may be tested to determine their accuracy in predicting values for the plurality of clinical-study metrics (e.g., enrollment rate, screening rate, screen failure ratio, etc.) for the particular clinical study 608 whose true values 610 for the metrics are known. In particular embodiments, testing may include using the category-specific ML models 656a, 656b, . . . , 656n to generate corresponding predicted values 658a, 658b, . . . , 658n (also individually and collectively referred to herein as 658). For instance, the category-specific ML model 656a is used to generate a predicted value 658a for a metric associated with the category for which the model 656a is trained, the category-specific ML model 656b is used to generate a predicted value 658b for a metric associated with the category for which the model 656b is trained, and the category-specific ML model 656n is used to generate a predicted value 658*n* for a metric associated with the category for which the model 656*n* is trained. Then predicted values 658 and the true values 610 for the metrics are compared 660 to determine an accuracy or confidence in the prediction of each of the metrics by each of the category-specific ML models 656. If the accuracy or confidence in predictions of a particular category-specific ML model 656 is greater than a certain threshold (e.g., above a certain confidence score), then the particular category-specific model 656 is deemed sufficiently trained and ready for deployment. Otherwise, the particular category-specific model 656 is re-evaluated qualitatively, its features re-engineered, and its training data quality further investigated and improved until the confidence in its predictions meets threshold criteria.

Similar to the baseline model 606, results of the testing of the category-specific ML models 656 may be stored in a data store for future access and/or retrieval or in in the form of a lookup table, such as the model performance lookup table 620, which is used at inference or run time by the model routing algorithm to select an appropriate model for a metric, as discussed elsewhere herein. In some implementations, based on the comparison 660 of the predicted and true values, performance benchmarks of each of the category-specific ML models 656 may be stored in the model performance lookup table 620. In particular embodiments, the performance benchmarks of a category-specific model 656 associated with a particular category may include a measure of difference in performance or accuracy in predicting each of the metrics in that category compared to the baseline model 606. In one example embodiment, the particular measure or indicator of this difference is in the form of percent difference in a root mean square error (RMSEhow rapidly patients are screened for participation in a study. In some embodiments, the screening rate may be defined as ratio of number of screened patients to the time between first site activation and last patient enrollment. Row 802*c* corresponds to screen failure ratio, which defines ratio of individuals screened, but not enrolled in a trial. In some embodiments, the screen failure ratio may be defined as number of screen failures per patients screened. Row 802*d* corresponds to regulatory approval duration, which defines how long the study has been waiting for regulatory approval. In some embodiments, the regulatory approval duration may be defined as time from internal protocol approval (FPA) to first regulatory approval (FRA). Row 802*e* corresponds to time to enrollment completion metric, which defines how long it takes to complete enrollment of patients. In other words, the time to enrollment completion may be defined as time from first regulatory approval (FRA) to last subject enrolled (LSE). 802*f* corresponds to time to first patient metric, which defines time from site activation to first enrollment. In other words, the time to first patient may be defines as site activation date (SAD) to first subject enrolled (FSE), with the median of this calculation taken across all study sites. Row 802*g* corresponds to dropout ratio metric, which defines ratio of patients who did not complete the study. In other words, the dropout ratio may be defined as 1−(number of patients who completed the study/number of patients enrolled). Row 802*h* corresponds to major protocol deviations per patient, which defines number of major protocol deviations divided by the number of enrolled patients. A protocol deviation may be defined as any change, divergence, or departure from the study design or procedures defined in the protocol. Row 802*i* corresponds to number of unique procedures. This is the number of actual (as opposed to planned) unique procedures that occur in the study, per patient, with the median taken across all patients.

Columns 804*a*, 804*b*, . . . , 804*i* in the model performance lookup table 800 correspond to the different category-specific ML models. Each cell 806 within each column represents a value indicating a measure of difference in performance of a particular category-specific ML model compared to the baseline model in predicting a particular metric. The measure of difference in performance or the value is calculated as follows:

$$\text{Percent difference in RMSE from baseline} = 100 *$$
$$(\text{filtered value} - \text{baseline value})/\text{baseline value}$$

Where, value represents the RMSE. So the baseline value in above equation is the RMSE for the baseline model 606, which is trained on the entire training dataset 602. Similarly, the filtered value in the above equation is the RMSE for a category-specific ML model, which is trained on a category-specific training dataset 654 (e.g., trained only on phase 1, or only on phase 1b, or only on ONC, etc.). Lower the percent difference (e.g., greater the negative value) for a particular metric, greater the accuracy of a particular category-specific ML model compared to the baseline model in predicting the particular metric. Here "X" in the table indicates that the percent difference in RMSE from baseline is greater than or equal to −10, which indicates that there is no significant improvement than the baseline model or that the accuracy of the baseline model is better than the category-specific ML model in predicting a particular metric.

As discussed elsewhere herein, the model performance lookup table 800 is used by the model routing algorithm at inference or run time to select an appropriate model from the baseline model and the plurality of category-specific models 804*a*, 804*b*, . . . 804*i* in predicting the plurality of clinical-study metrics 802*a*, 802*b*, . . . , 802*i*. By way of an example, for a study with phase 1b+ONC, the model routing algorithm may use the table 800 to look up RMSE percent difference 806 in the phase 1b 804*b* column and ONC column 804*f*, and compare the values in the two columns 804*b* and 804*f* to determine whether to select the phase 1b model, the ONC model, or the baseline model in predicting each metric. For enrollment rate metric 802*a*, the model routing algorithm based on the comparison of the two columns 804*b* and 804*f* may determine that the RMSE is 87.41 percent lower (or in other words the accuracy is better) when the prediction is done by the phase 1b model compared to the baseline model and that there is no significant improvement when using the ONC model (as denoted by X) or its prediction is worse than the baseline model. As such, the model routing algorithm may select phase 1b model for predicting the enrollment rate metric 802*a*. Similarly, for the screening rate metric 802*b*, the model routing algorithm based on the comparison of the two columns 804*b* and 804*f* may determine that the RMSE percent difference from baseline for the phase 1b model, −83.12 percent, lower than the RMSE percent difference from baseline for the ONC model, −23.77 percent. This indicates that the phase 1b model is the best performing model compared to the baseline and the ONC models and therefore, the model routing algorithm selects phase 1b model for predicting the screening rate metric 802*b*. Similarly, the model routing algorithm may select appropriate models for rest of the metrics 802*c* to 802*i* and create a routing dictionary of selected models as follows:

| Metric | Model |
|---|---|
| ENROLLMENT_RATE | Phase 1b |
| SCREENING_RATE | Phase 1b |
| SCREEN_FAIL_RATIO | Baseline |
| . . . | . . . |
| MEDIAN_NUM_PROCEDURES_ACTUAL | ONC |

Validation of Model Routing

Once the various models, including the baseline model and a plurality of category-specific ML models, are trained and deployed as discussed above in reference to FIG. 2, a validation procedure may be performed to validate that the model routing algorithm is working as intended. Provided below is a validation procedure to validate the model routing:

1. For each metric (e.g. enrollment rate) and for each category (e.g., phase/TA):
   (a) get predictions for baseline (unfiltered data) and for the model filtered by the category.
   (b) find intersection between a test set of the baseline model and a test set of the filtered model, where the test set is random subset of the training set that was not seen by the model at training time.
   (c) remove studies that will be routed to the model filtered by the category from the main training dataset (e.g., training dataset 602).
   (d) build the models, baseline and for routing, using the remaining studies in the training dataset.
   (e) predict the metric for the studies that were removed.
   (f) check if predicted value by the category-specific model is closer to the true value than the predicted value by the baseline model or vice versa, and calculate the fold improvement:
      (i) For regular filtering
      (ii) For routing
   (g) Count the number of concordant samples between regular filtering and routing
2. Calculate the total percentage of samples with predicted values by the category-specific model closer to the true values than the baseline model for:
   a. Regular filtering
   b. Routing
3. Calculate percentage of samples that show concordance between regular filtering and routing.
4. Perform a Wilcoxon's rank sum test comparing the [log base 10] absolute difference from true values to the baseline predictions and from the true values to the:
   a. filtered predictions, to show that filtering does indeed produce predictions closer to the true values than baseline.
   b. routed predictions, to show the same for routing.

Figure 9:
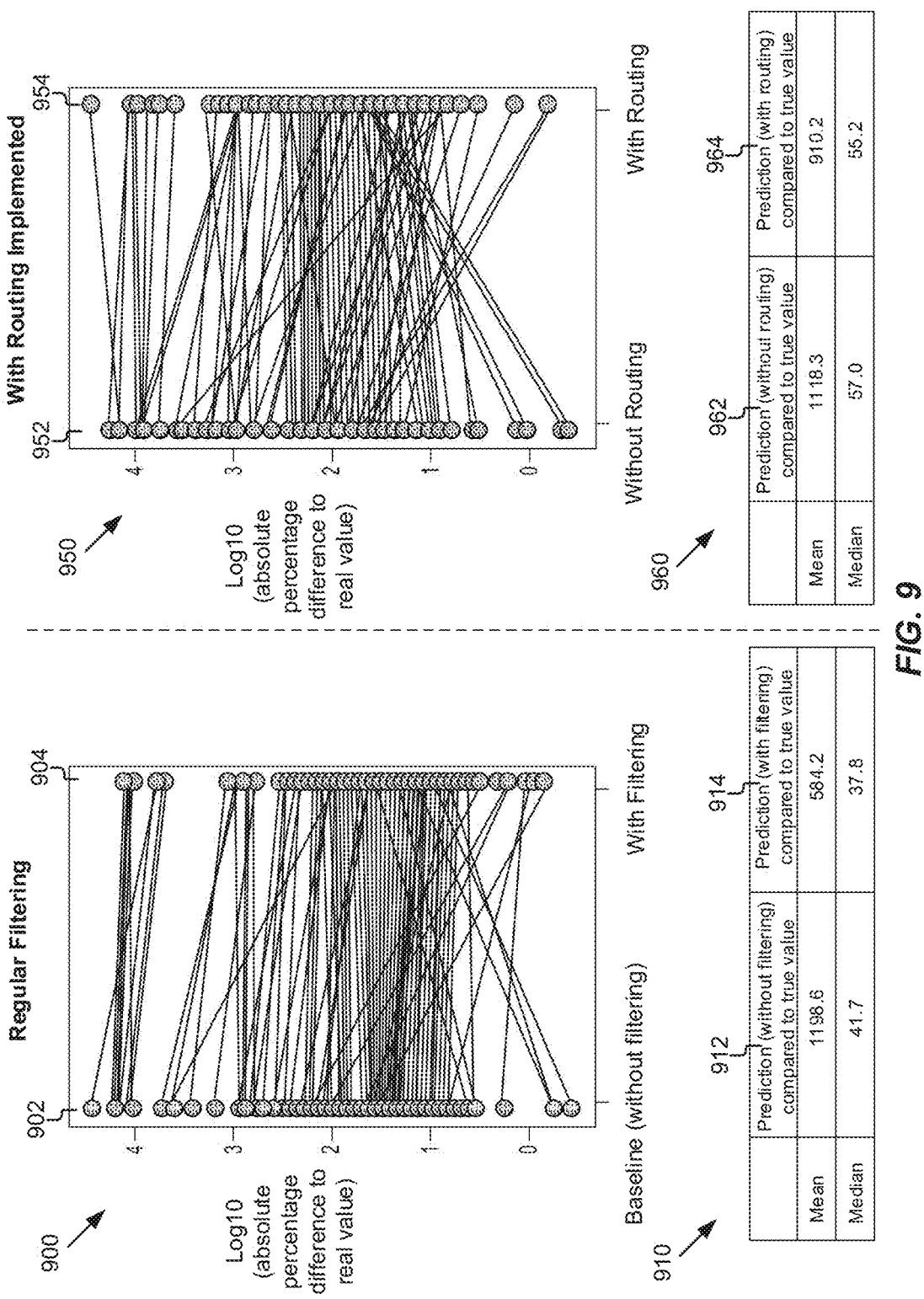
FIG. 9 illustrates an example validation of a model routing algorithm based on comparing results with regular filtering and with model routing.

FIG. 9 illustrates an example validation of a model routing algorithm based on comparing example results with regular filtering and with model routing. It should be noted that an example internal data set of clinical trials was used for purposes of this example validation. Chart 900 on the left shows a comparison of absolute percentage difference to true values from the baseline predictions (indicated by 902) and from the filtered predictions (indicated by 904). In particular embodiments, the chart 900 may be produced based on step 4 of the validation procedure discussed above. Table 910 shows the mean and median values for the baseline predictions (column 912) and the filtered predictions (column 914). As can be seen from the table 910, the filtered predictions are relatively closer to the true values, as indicated by lower mean and median values of the filtered predictions compared to the baseline predictions.

Similarly, chart 950 on the right shows a comparison of absolute percentage difference to true values from the baseline predictions (indicated by 952) and from the routed predictions i.e., with model routing implemented (indicated by 954). In particular embodiments, the chart 950 may be produced based on step 4 of the validation procedure discussed above. Table 960 shows the mean and median values for the baseline predictions (column 962) and the routed predictions (column 964). As can be seen from the table 960, the routed predictions are relatively closer to the true values, as indicated by lower mean and median values of the routed predictions compared to the baseline predictions.

Since both the filtered predictions and routed predictions are relatively closer to the true values than the baseline predictions, there is concordance between the regular filtering and model routing, and hence the model routing algorithm is determined to be working correctly or as intended.

Figure 10:
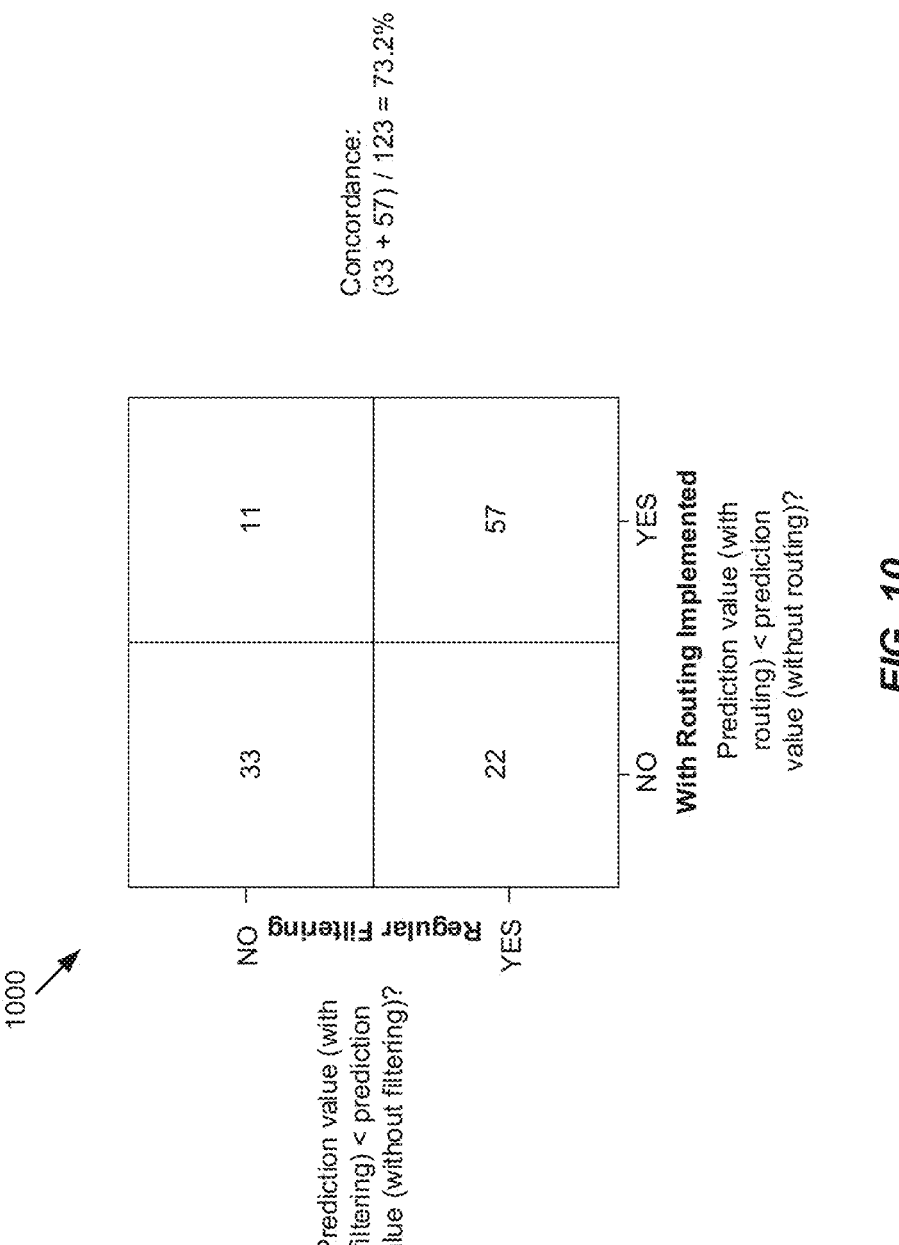
FIG. 10 illustrates an example chart showing concordance between results of regular filtering and of model routing for validating a model routing algorithm.

FIG. 10 illustrates an example chart 1000 showing concordance between results of regular filtering and of model routing for validating a model routing algorithm. In particular, the chart 1000 shows an example number of samples for which the filtered predictions (e.g., predictions with regular filtering) and routed predictions (e.g., predictions with model routing implemented) both either have predictions better than baseline predictions or worse than the baseline predictions. As shown, there are 33 samples out of total of 123 samples for which the both the filtered and routed predictions are better than the baseline predictions, and there are 57 samples out of total of 123 samples for which the both the filtered and routed predictions are worse than the baseline predictions. The percentage of samples that show concordance between regular filtering and routing comes out to 73.2%. In particular embodiments, the percentage concordance may be calculated based on step 3 of the validation procedure discussed above. In some embodiments, the percentage concordance of samples may be used to validate the model routing algorithm. For instance, if the percentage concordance between the regular filtering and model routing is greater than a certain threshold (e.g., greater than 70%), then the model routing algorithm is determined to be working correctly or as intended.

Robust Outlier Detection and Removal

When training a machine-learning model (e.g., a baseline model, a category-specific ML model) using a training dataset (e.g., training dataset 602), outliers in the training dataset may reduce the quality of the model's predictions. As such, a pre-processing step before training a model may be required to remove outliers in the training dataset. A standard way to remove outliers is to convert the data to z scores based on a mean and standard deviation, and remove all values with z scores whose absolute values are at least 3 standard deviations above the mean. This method of removing outliers based on standard z scores, while commonly used suffers from a lack of robustness when extreme outliers in the dataset end up influencing the mean and standard deviation used to detect outliers, thus allowing less-extreme outliers to remain in the dataset, and therefore reduce the quality of the model's predictions. As such, there is a need for an improved method for outlier detection and removal.

Figure 11:
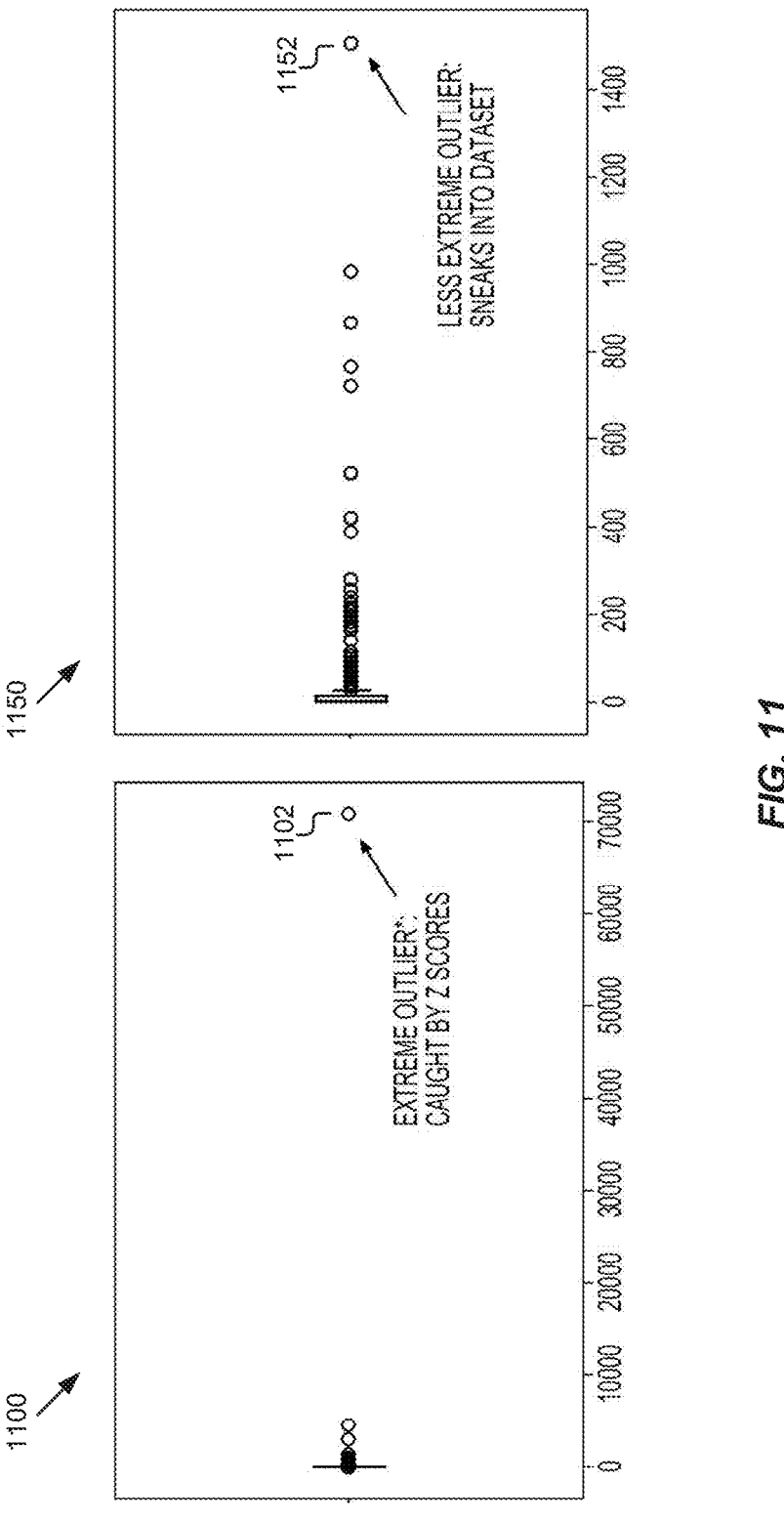
FIG. 11 illustrates an example outlier detection using a standard z-score technique.

FIG. 11 illustrates an example outlier detection using the standard z-score technique, discussed herein. Chart 1100 shows an example extreme outlier 1102 that is caught based on z scores i.e., data points with z scores whose absolute values are at least 3 standard deviations above the mean are detected as outliers in the dataset. However, as mentioned above, these extreme outliers in the dataset end up influencing the mean and standard deviation used to detect outliers, thus allowing less-extreme outliers to remain in the dataset. Chart 1150 shows an example of a less extreme outlier 1152 that is left in the dataset due to the influence of the extreme outliers. It should be noted that both the charts 1100 and 1150 show the same datasets, but with difference x-axis ranges. Chart 1150, in particular, shows a narrower range to highlight the less-extreme outlier 1152, which is not easily visible in the wider range of the chart 1100.

One solution to fix the above problem associated with the standard z-score technique is to remove outliers based on median instead of the mean, since the median is less influenced by extreme outliers. This method is known as a modified z-score technique of outlier detection and removal. In the modified z-score technique, the data is converted to modified z scores based on the median and median absolute deviation (MAD), and those data points that have absolute value at least 3.5 median absolute deviations above the median are considered outliers. However, there are still problems associated with removing outliers based on this modified z-score technique. For instance, the modified z-score technique suffers from being too aggressive in removing data points that are not close to the median. An obvious way to remedy this is to change the default threshold of 3.5 and increase it so that less data is lost.

Particular embodiments fix the above problems associated with the standard z-score and modified z-score techniques by providing an improved method for data-loss-conscious outlier detection and removal. Instead of arbitrarily changing the threshold for outlier detection, the improved method iteratively increases the threshold, and checks how much data would be lost compared to using a standard method (e.g., using standard z scores). If the amount of data lost is considered unacceptable or more than an acceptable limit (e.g., loss of more than 1% of the dataset), the threshold is increased by a small amount, and the process is repeated until the amount of data lost is within the acceptable limit. In summary, the improved method allows for more robust detection of outliers (to prevent extreme values from obscuring less-extreme values that should still be removed), and also for programmatically setting a threshold that prevents excessive data loss from outlier removal. By properly removing true outliers while including all non-outlier data, the improved method, when used to pre-process a training dataset, improves the predictions of the model trained on this dataset.

Below is an example of the high-level steps that may be involved to iteratively obtain a threshold (e.g., adaptive threshold) for outlier detection and removal:

1. Set the tolerance for data loss (e.g. 1%) and amount by which to increment a threshold (e.g. 0.5).
2. Set the baseline threshold for modified z scores (e.g., default baseline threshold is set to 3.5).
3. Drop outliers from the data using a first scoring technique (e.g., standard z-score technique) and record the number of rows remaining.
4. In a loop:
   a. Drop outliers from the data using a second scoring technique (e.g., modified z-score technique) and current threshold.
   b. Check how many rows remain compared to the number of rows from step 3 and get the percent difference: (rows in step 3–rows in step 4a)/rows in step 3.

c. If the percent difference is higher than the data loss tolerance, increment the threshold and repeat step 4. Otherwise, stop.

Once the adaptive threshold is obtained based on the iterative process discussed above, the adaptive threshold may be used to remove outliers from a training dataset (e.g., training dataset 602). Below is an example of the high-level steps that may be involved to remove outliers using the adaptive threshold:

1. Get the median of the dataset.
2. Get the median absolute deviation (MAD) of the dataset.
3. To avoid dividing by zero: if the MAD is zero (e.g., meaning there's not much variance in the data so modified z scores are unlikely to confer an additional benefit), simply use the standard z scores method.
4. Otherwise, calculate the modified z score using an existing formula which uses the median and MAD.
5. Detect data points in the training dataset with modified z scores with absolute values greater than the adaptive threshold as outliers.
6. Remove the outliers.

It should be noted that the above steps for obtaining an adaptive threshold and removing outliers using the adaptive threshold are merely high-level steps of the improved method discussed herein, and detailed description on each of these steps is further discussed with respect to FIGS. 17 and 18.

Figure 12:
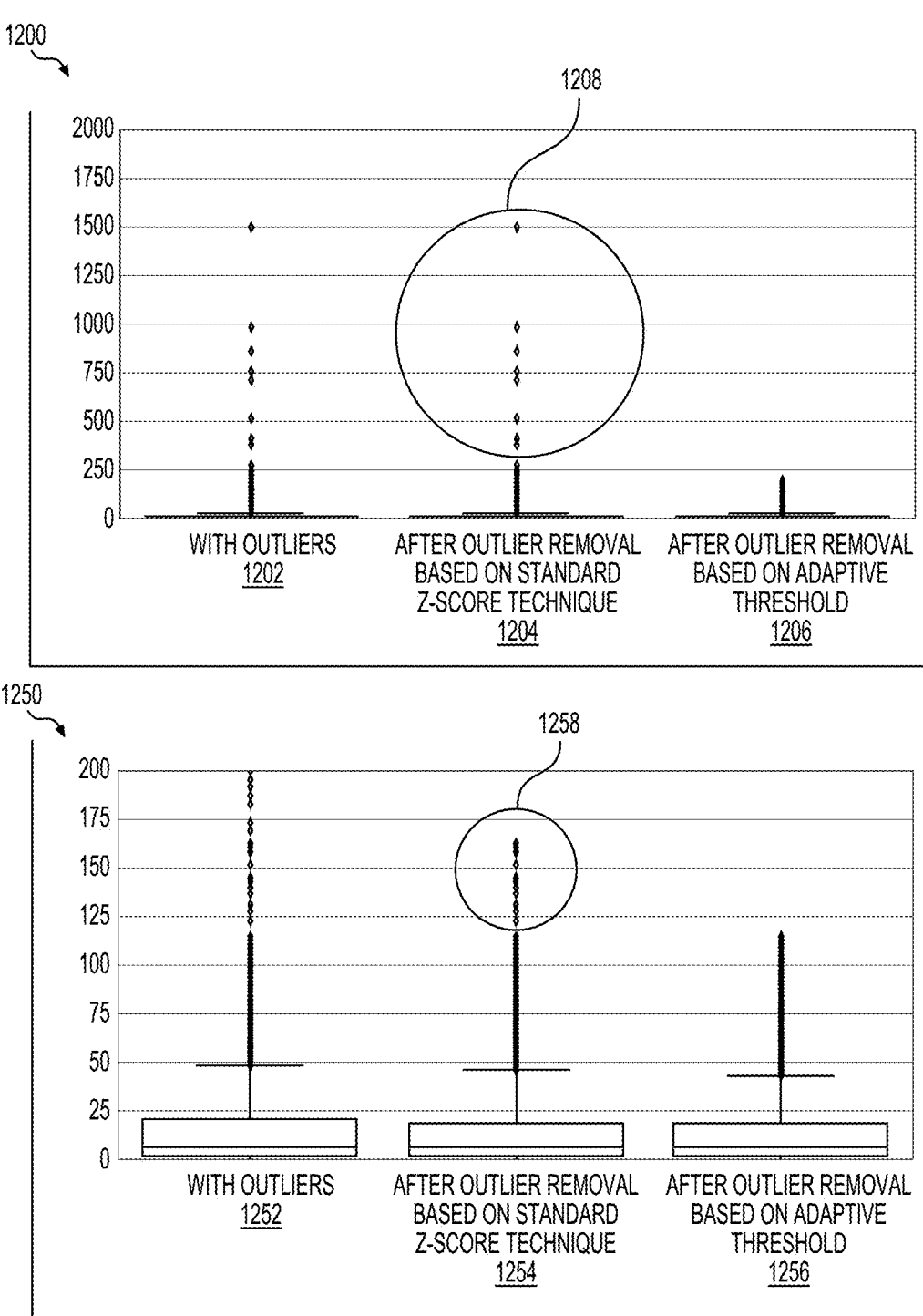
FIG. 12 illustrates an example of outlier removal from a training dataset using an improved method of outlier detection and removal discussed herein.

FIG. 12 illustrates an example of outlier removal from a training dataset using the improved method of outlier detection and removal discussed herein. In particular, FIG. 12 includes charts 1200 and 1250 each showing comparison of outlier removal using an existing method (e.g., based on standard z scores) and the improved method (e.g., based on adaptive threshold). Specifically, chart 1200 shows outlier removal from training data associated with enrollment rate metric. Reference numeral 1202 represents data points without any outlier removal method applied (i.e., data points with outliers), reference numeral 1204 represents data points resulting after applying the standard z-score technique discussed herein, and reference numeral 1206 represents data points results after applying the modified z-score technique and using the adaptive threshold. As can be seen from the chart 1200, considerable amount of data points 1208 are detected as outliers and removed from the training data using the improved method discussed herein as compared to the existing z-score based method.

Chart 1250 shows outlier removal from training data associated with screening rate metric. Similar to chart 1200, reference numeral 1252 represents data points without any outlier removal method applied (i.e., data points with outliers), reference numeral 1254 represents data points resulting after applying the standard z-score technique discussed herein, and reference numeral 1256 represents data points results after applying the modified z-score technique and using the adaptive threshold. As can be seen from the chart 1250, additional data points 1258 are detected as outliers and removed from the training data using the improved method that were unable to be caught or detected by the existing z-score based method.

FIG. 13 illustrates example results for different metrics before and after applying the improved method of outlier detection and removal discussed herein. In particular, FIG. 13 illustrates a table 1300 with a first column 1302 containing RMSE values associated with a baseline model in predicting 9 metrics before the outlier removal and a second column 1304 containing RMSE values associated with the baseline model in predicting the 9 metrics after the outlier removal using the improved method discussed herein. As mentioned earlier, a lower RMSE value indicates a reduced error in predicting a value for a metric or in other words a predicted value by the baseline model is closer to a true value. Conversely, a higher RMSE value indicates an increased error in predicting a value for a metric or in other words a predicted value by the baseline model is far from a true value. As can be seen from the table, the RMSE values for metrics 4, 6, 8, and 9 are considerably reduced after the outlier removal from a training dataset that was used to train the baseline model in predicting these metrics.

FIG. 14 illustrates example thresholds determined for different metrics for outlier removal and amount of data loss compared to standard z-score technique in outlier removal using the thresholds determined for these metrics. In particular, FIG. 14 illustrates a table 1400 with a first column 1402 containing a percent data loss value compared to z scores after outlier removal for each of 9 metrics and a second column 1404 containing a modified z-score threshold that was determined for each of the 9 metrics using the process of obtaining an adaptive threshold discussed herein. As can be seen from the table 1400, instead of a default threshold value of 3.5 for all the 9 metrics as used in a standard or modified z-score technique for outlier removal, different threshold values are determined for different metrics. Also, the percent data loss for each of these metrics are within their acceptable limit (e.g., less than 1% data loss).

Example User Interfaces

FIGS. 15A-15H illustrate example graphical user interfaces that are associated with a clinical study tool discussed herein. As mentioned elsewhere herein, the clinical study tool may be a machine-learning tool for predicting multiple operational metrics for a clinical study or trial based on protocol eligibility criteria text and study metadata. The clinical study tool may be used by clinical scientists and other users during a protocol design phase, as shown and discussed in reference to FIG. 4. The model routing algorithm discussed herein may be used in the clinical-study tool for making various predictions on a new clinical study. For example, given user inputs via a graphical user interface of the clinical study tool, such as selection of a therapeutic area, a study phase, a clinical-study metric, etc., the model routing algorithm may select an appropriate trained model for predicting values for that clinical-study metric. The selected model by the model routing algorithm may output a prediction for an enrollment rate (e.g., patients/month) metric. Similarly, different models may be selected for predicting other clinical-study metrics, such as screening rate of patients, a screen failure ratio, a patient dropout ratio, etc. Using the predicted values by the models for the clinical-study metrics, various predictions or data driven insights, such as operational burden measures, site burden measures, patient burden measures, etc. may be generated for display on a graphical user interface of the clinical-study tool, as shown, for example, in FIG. 15H.

Figure 15A:
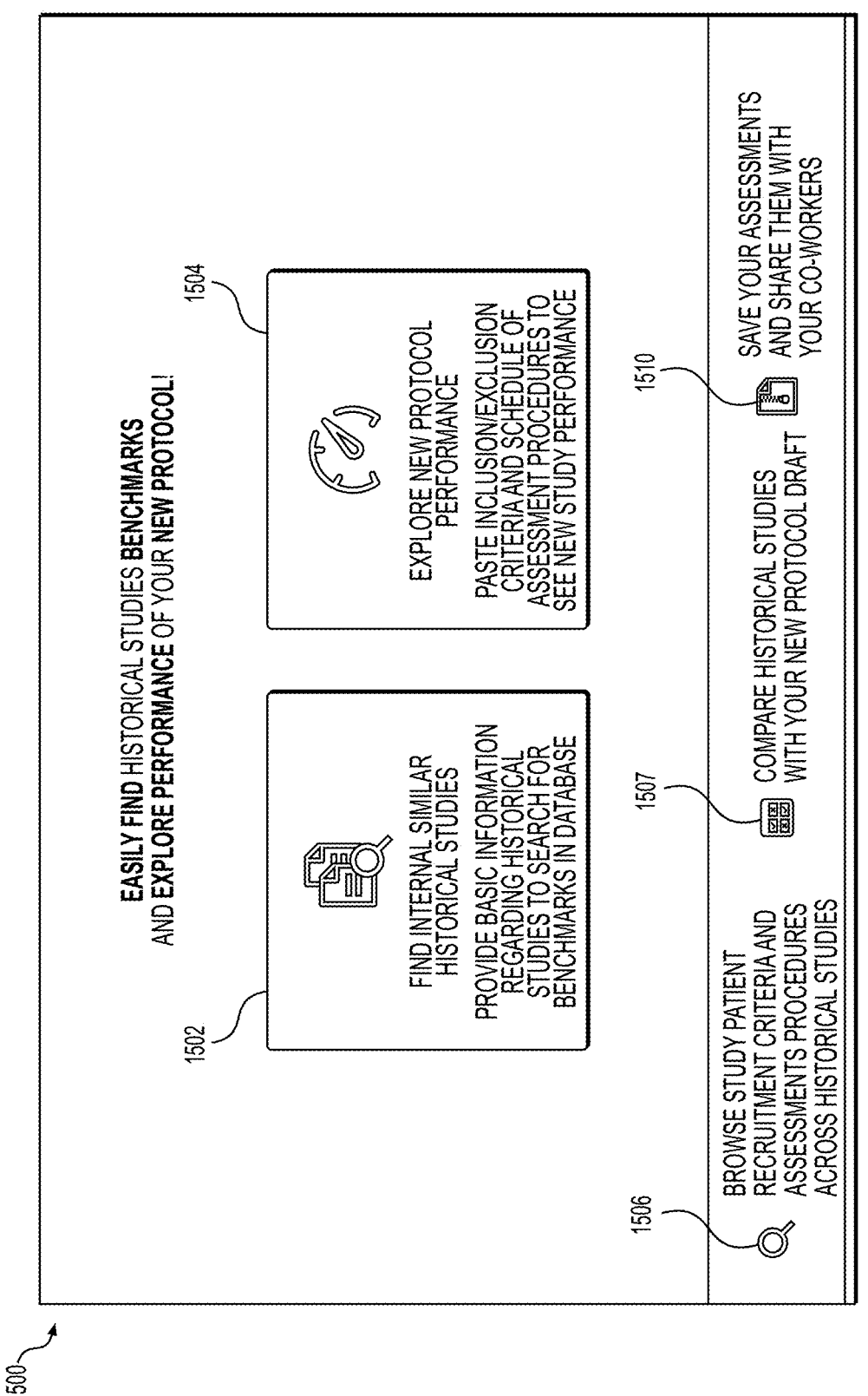
FIGS. 15A-15H illustrate example graphical user interfaces that are associated with a clinical study tool discussed herein.

FIG. 15A illustrates an example graphical user interface 1500 of a main menu of the clinical study tool. As depicted, the menu consists of various options including an option 1502 to find internal similar historical studies of patients by receiving user information (e.g., as shown and discussed in FIGS. 15B and 15C) regarding historical studies to search for benchmarks in a database; an option 1504 to explore new protocol performance (e.g., as shown in FIGS. 15F and 15G) based on user-defined inclusion/exclusion criteria and schedule of assessment procedures to see new study performance, an option 1506 to browse study patient recruitment criteria and assessments procedures across historical studies, an option 1508 to compare historical studies with a new protocol draft (e.g., as shown in FIGS. 15E and 15G), and an option 1510 to save assessment and share them with other users, such as co-workers or other clinical scientists.

Figure 15B:
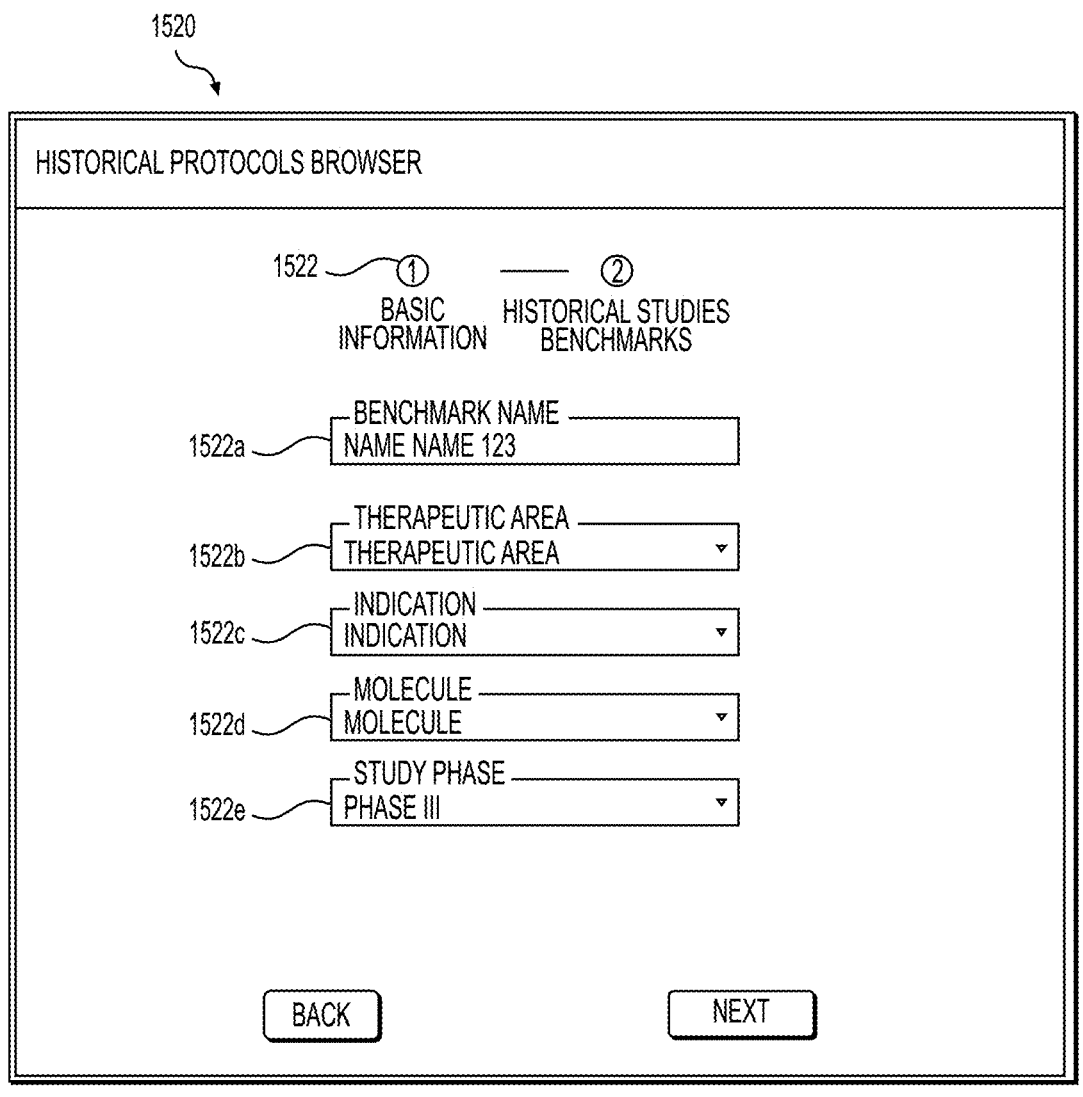

FIG. 15B illustrates an example graphical user interface 1520 showing basic user inputs that may be received in a historical protocols browser associated with the clinical study tool. In some embodiments, the graphical user interface 1520 may be displayed in response to selecting the option 1502, as shown in FIG. 15A. The historical protocols browser may be used to browse or find internal similar historical studies of patients based on basic information 1522 received from a user. For example, clinical scientists may use this feature to assess or evaluate historical clinical studies of patients and associated information that would help them in designing new protocols or studies. As depicted, the basic information 1522 that may be received from a user in order to find historical protocols or studies may include, for example, a benchmark name 1522a, a therapeutic area 1522b (e.g., oncology, neurology, etc.), an indication 1522c, a molecule 1522d, and a study phase 1522e (e.g., phase 1, phase 2, phase 3, etc.).

Figure 15C:
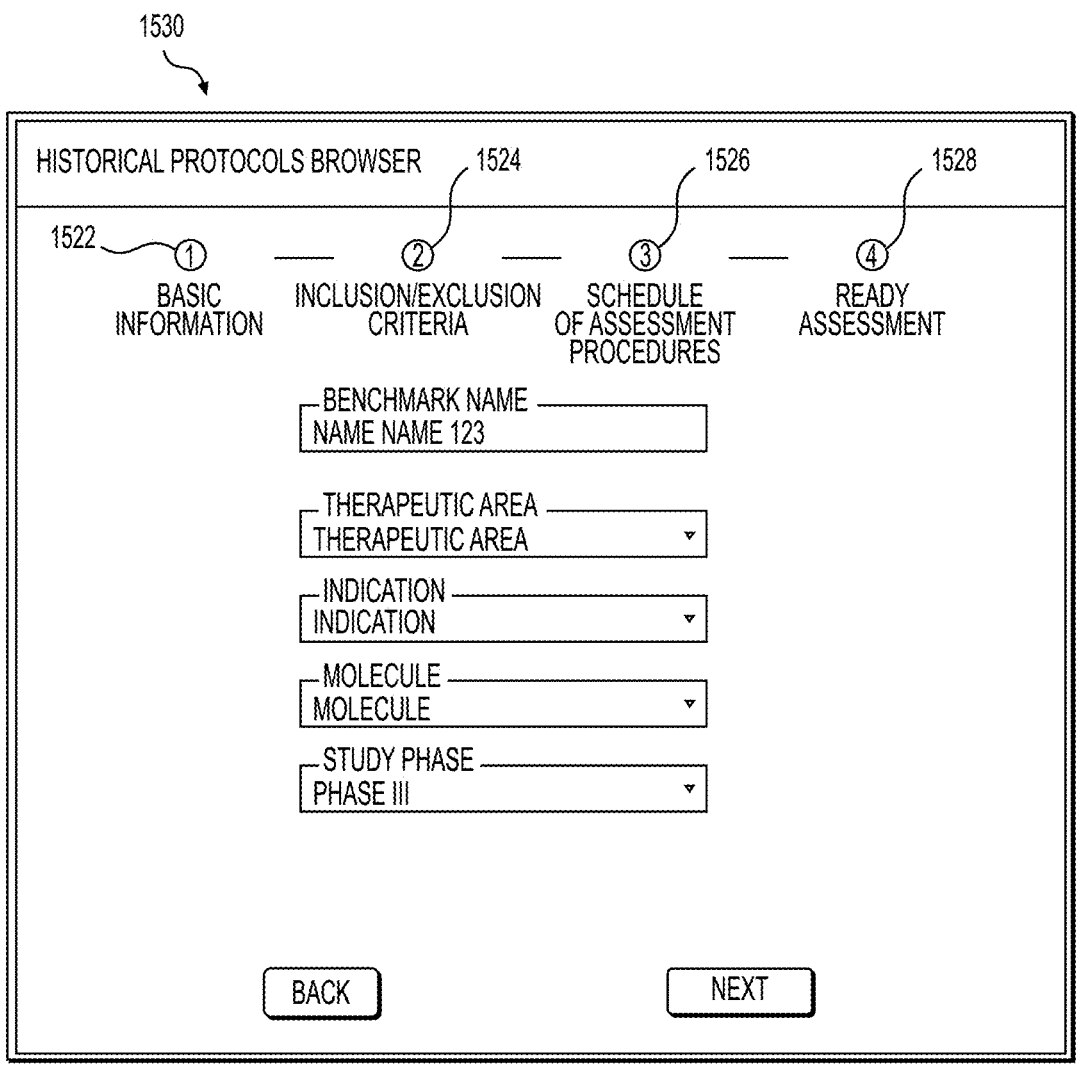
Figure 15D:
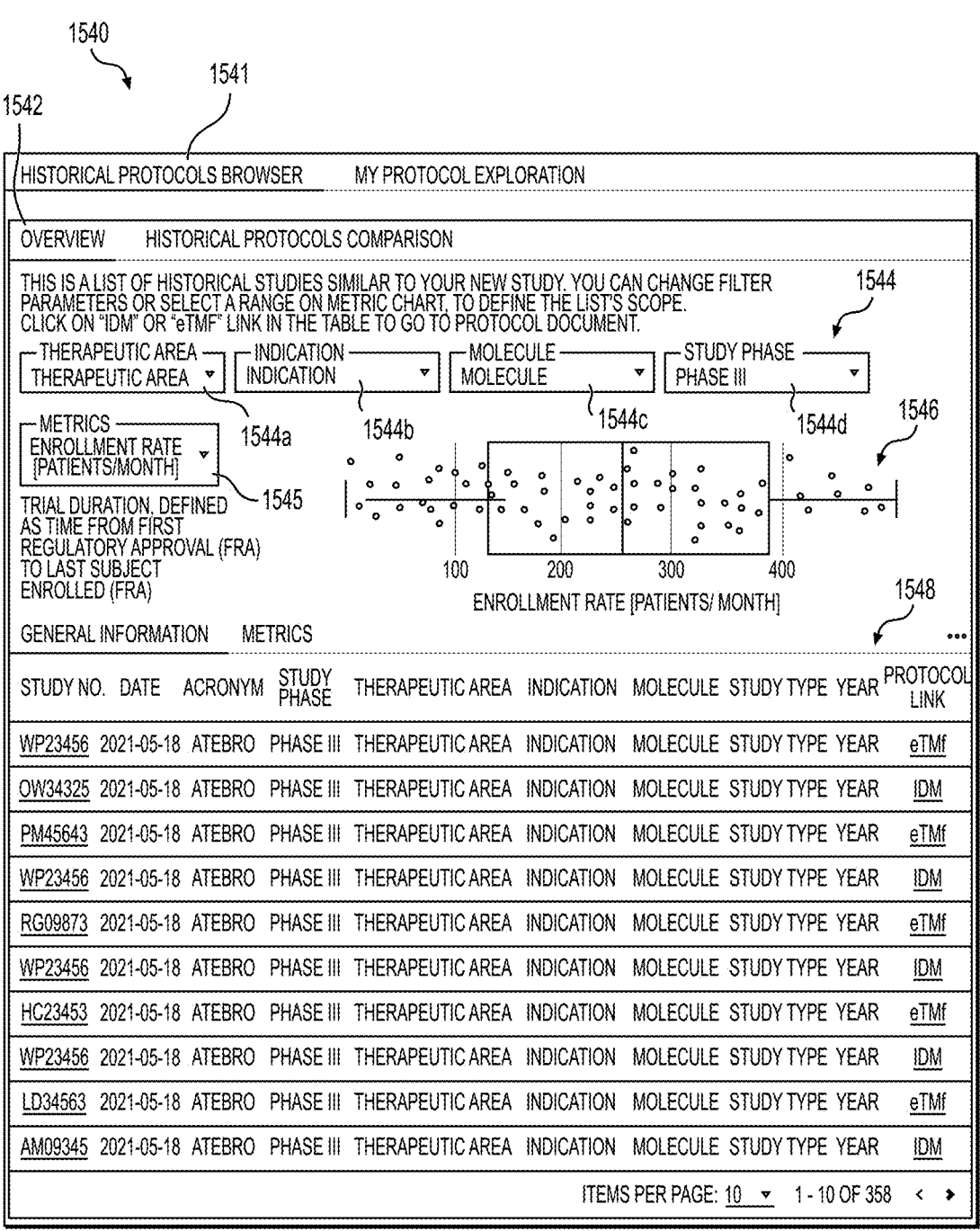
Figure 15E:
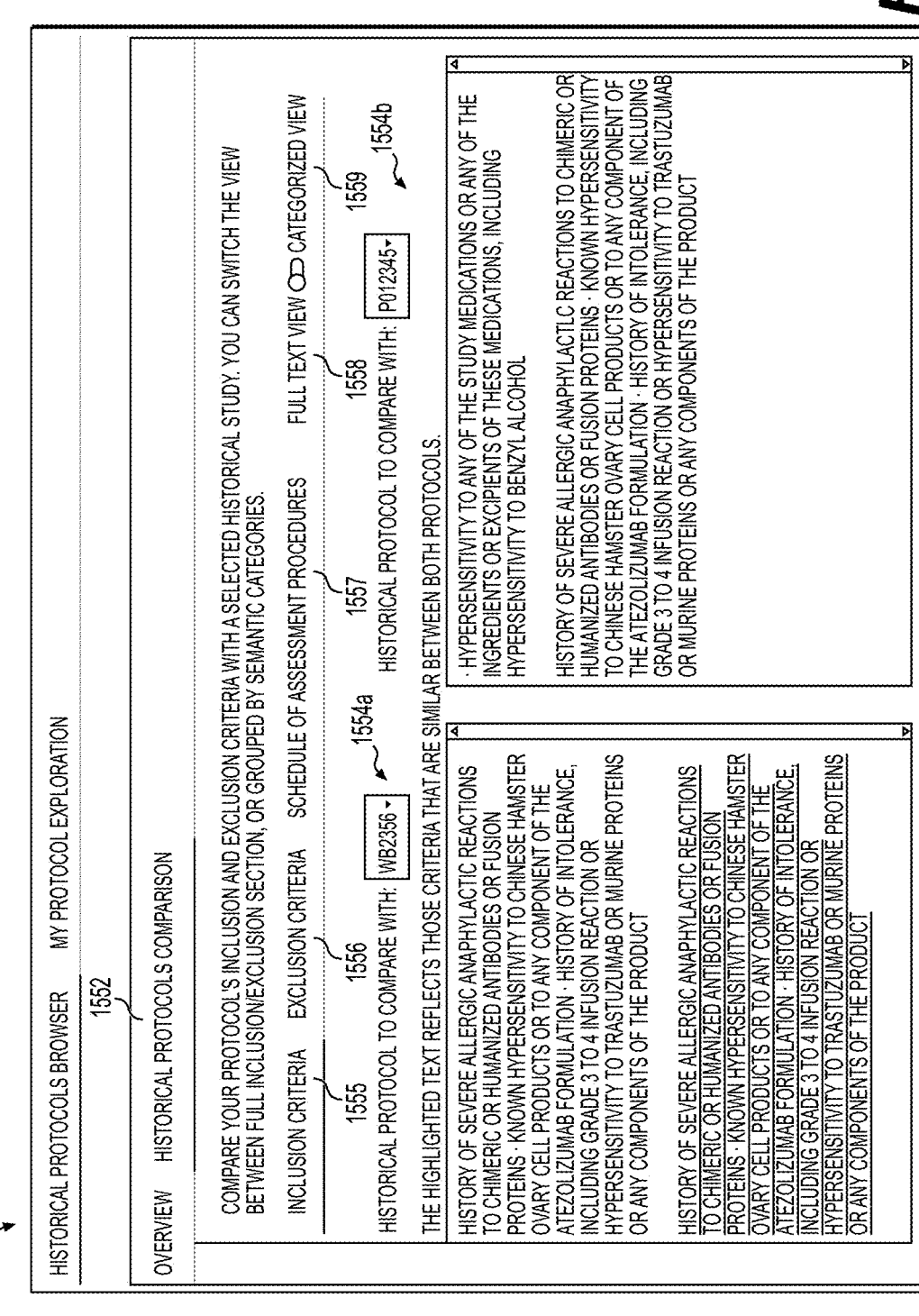
Figure 15F:
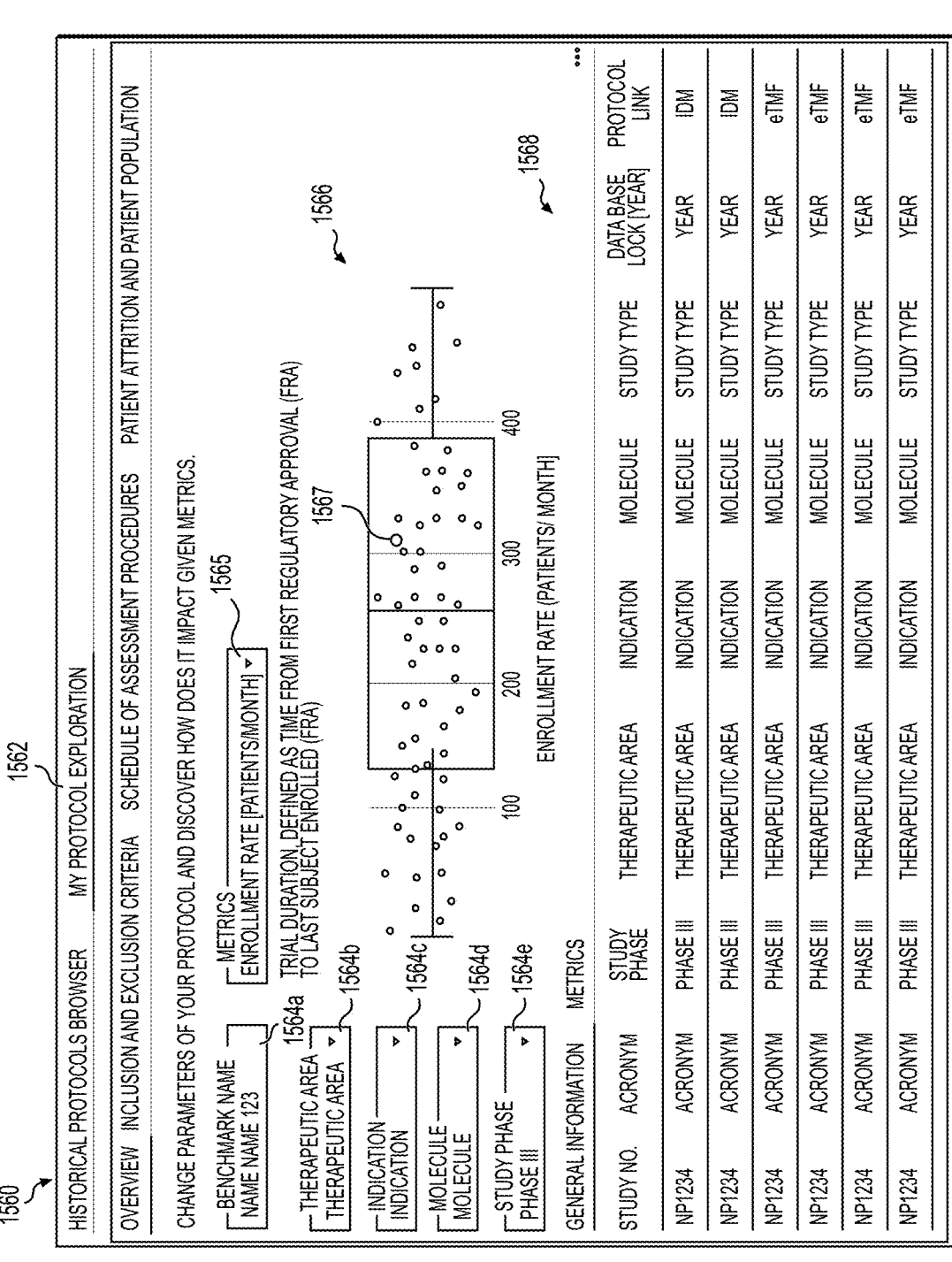
Figure 15G:
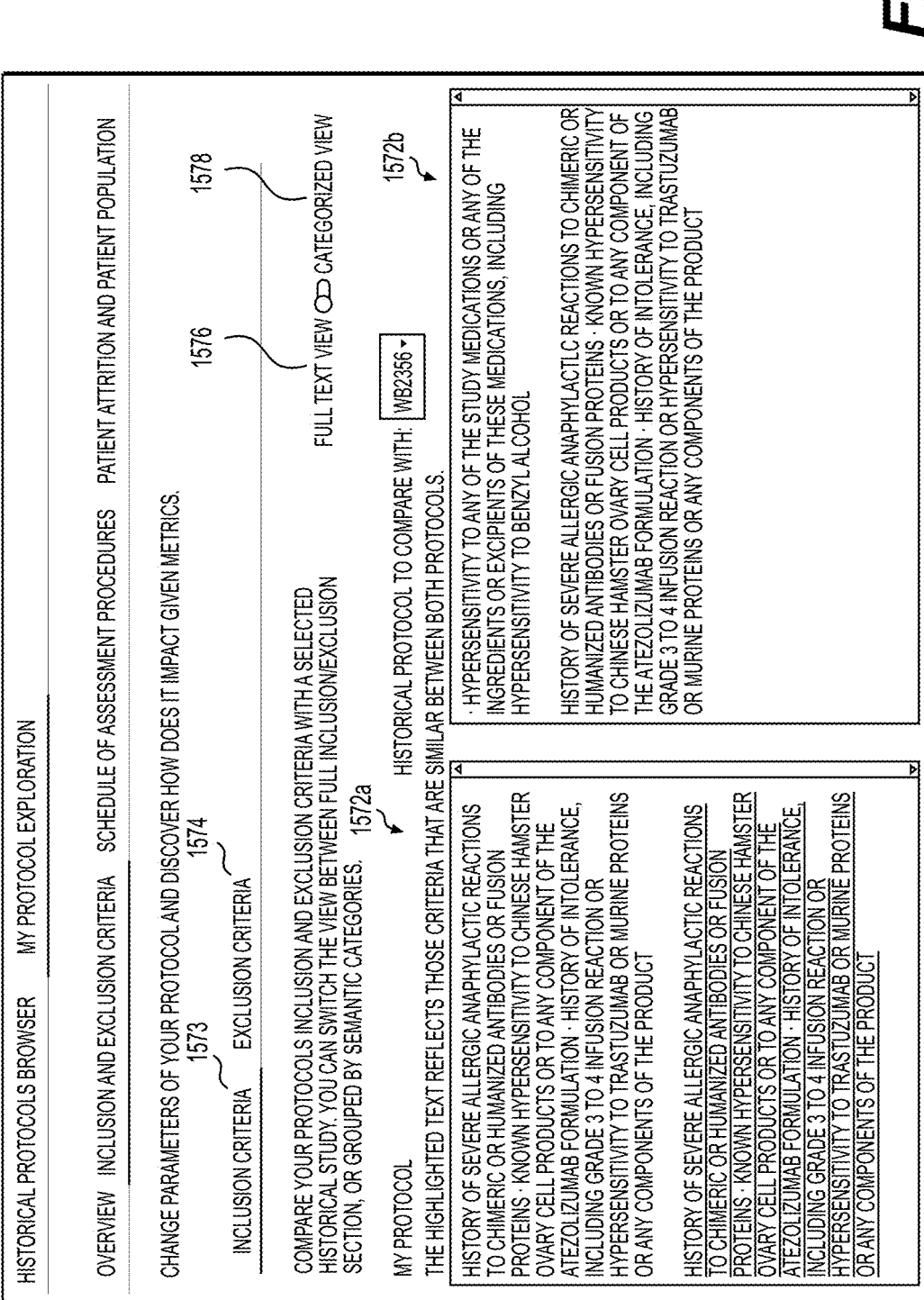
Figure 15H:
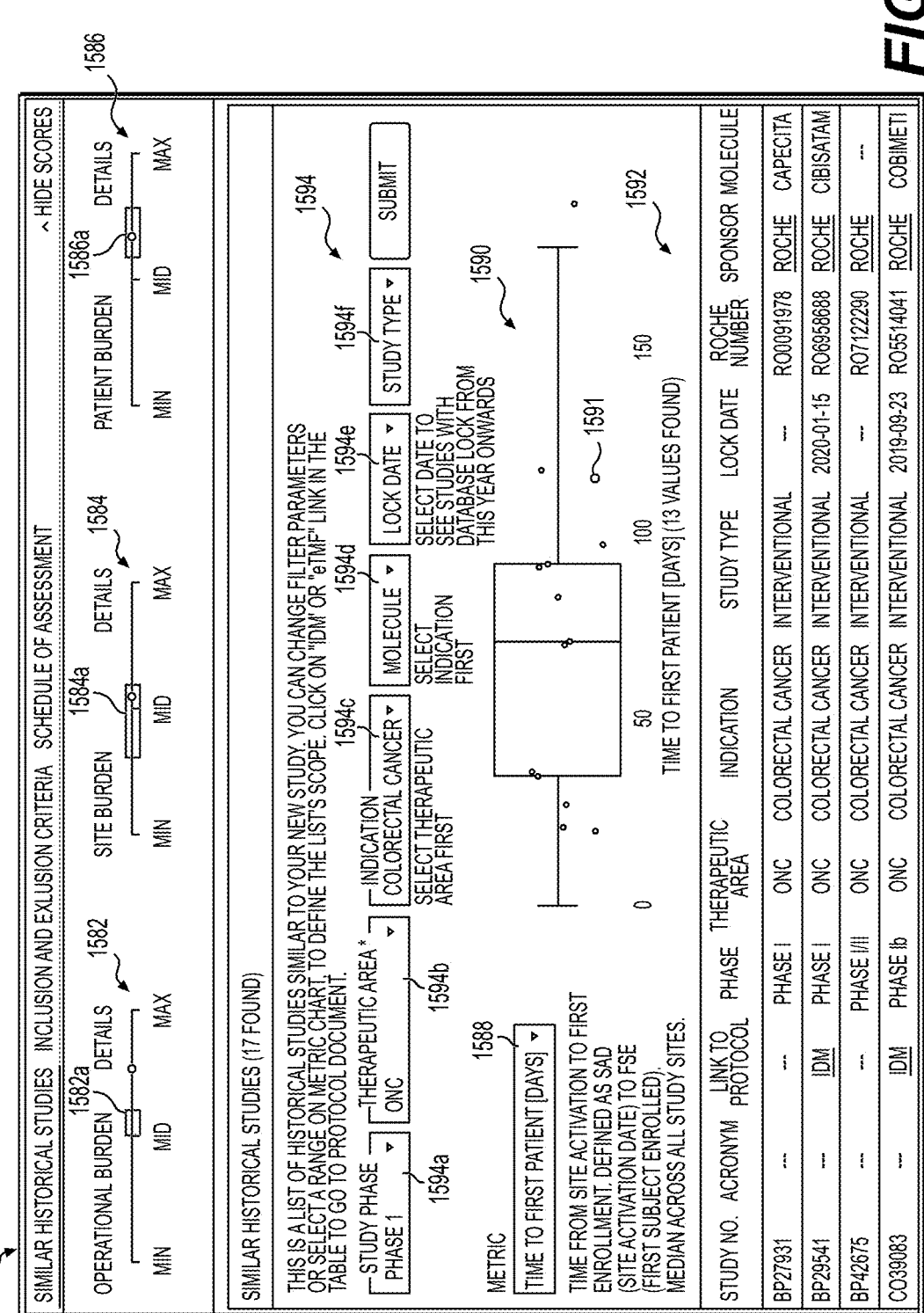

FIG. 15C illustrates an example graphical user interface 1530 showing advanced user inputs that may be received in the historical protocols browser associated with the clinical study tool. Here, in addition to the basic information 1522, the graphical user interface 1530 may also enable a user to provide additional information, such as various inclusion/exclusion criteria 1524, schedule of assessment procedures 1526, and one or more other inputs to make a protocol or study ready for assessment 1528. For instance, in the inclusion/exclusion criteria 1524, the graphical user interface 1530 may enable the user to specify inclusion criteria and inclusion criteria of their prospective study, where it will be analyzed using natural language processing (NLP) methods and mapped to discrete features which indicate categories of eligibility criteria, and counts for the number of times each category appears in a protocol. These categories and counts are used as features in the downstream machine learning models used to predict the plurality of metrics mentioned previously. In the schedule of assessment procedures 1526, the graphical user interface 1530 may enable the user to specify list of assessment procedures ("schedule of assessments") that a patient will need to undergo during a clinical study or trial. These procedures are similarly analyzed and categorized using NLP methods, and the resulting counts and indicator variables for categories of procedures are used as features in the downstream machine learning models used to predict the plurality of metrics mentioned previously. In the ready assessment 1528 tab, assessment of the prospective study protocol, including the output and data driven insights, is shown, similar to FIG. 15H.

FIG. 15D illustrates an example graphical user interface 1540 showing an overview 1542 of information that is provided by the historical protocols browser 1541 of the clinical study tool. In some embodiments, the graphical user interface 1540 may display or provide the overview 1542 in response to receiving user inputs, including basic user inputs as shown in FIG. 15B or advanced user inputs as shown in FIG. 15C. For instance, based on user inputs 1544 including a therapeutic area 1544a, an indication 1544b, a molecule 1544c, and study phase 1544d, the graphical user interface 1540 may display or provide information associated with various metrics. As depicted, the current information displayed in the overview 1542 relates to the enrollment rate (patients/month) metric. The graphical user interface 1540 may enable the user to switch to another metric and display information for that metric using a dropdown menu 1545. For example, the graphical user interface 1540 may display information relating to screening rate metric based on user selection of that metric using the dropdown menu 1545. As depicted, the overview 1542 includes a chart 1546 showing enrollment rate of patients and other similar historical studies 1548 associated with similar user inputs 1544.

FIG. 15E illustrates an example graphical user interface 1550 showing historical protocols comparison 1552 between two example studies or protocols 1554a and 1554b. For instance, using the historical protocols comparison 1552, the graphical user interface 1550 may enable a user to compare the two protocols or studies 1554a and 1554b based on inclusion criteria 1555, exclusion criteria 1556, or schedule of assessment procedures 1557. Also, the graphical user interface 1550 may enable the user to choose or switch between a full text view 1558 (as currently displayed) or a categorized view 1559 to view studies or protocols grouped by semantic categories. As depicted, the historical protocols comparison 1552 currently shows the comparison between 1554a and 1554b based on inclusion criteria 1555. In some embodiments, the graphical user interface 1550 is displayed in response to a user selecting option 1508 from the main menu (e.g., as shown in FIG. 15A) of the clinical study tool.

FIG. 15F illustrates an example graphical user interface 1560 associated with a protocol exploration feature 1562 of the clinical study tool. The protocol exploration feature 1562 may allow a user to assess/evaluate their current protocol or a new protocol that they may be designing. For instance, the graphical user interface 1560 may enable the user to change various parameters or inputs 1564a, 1564b, 1564c, 1564d, and 1564e of their protocol in real time and discover how it impacts given metrics. The graphical user interface 1560 may further enable the user to choose a desired metric from a dropdown menu 1565. Based on the provided parameters or inputs 1564a-1564e, the graphical user interface 1560 may display a chart 1566 containing a predicted value and other values associated with historical studies for a metric. For example, as shown, a predicted value 1567 for the enrollment rate metric may be provided in the chart 1566. The predicted value 1567 may be determined using one of a baseline model or a category-specific ML model by the model routing algorithm, as discussed elsewhere herein. Also, similar to the graphical user interface 1540, the graphical user interface 1560 may display or provide other historical studies 1568 associated with similar user inputs or parameters 1564a-1564e. In some embodiments, the graphical user interface 1560 is displayed in response to a user selecting option 1504 from the main menu (e.g., as shown in FIG. 15A) of the clinical study tool.

FIG. 15G illustrates an example graphical user interface 1570 showing protocols comparison between a user's protocol 1572a and a historical protocol 1572b. The graphical user interface 1570 is similar to the graphical user interface 1550, however instead of comparing two historical protocols, here the graphical user interface 1570 is used to compare a user's current or new protocol 1572a that they may be designing with a historical protocol 1572b. The graphical user interface 1570 may enable the user to compare the two protocols 1572a and 1572b based on inclusion criteria 1573 or exclusion criteria 1574. Also, the graphical user interface 1570 may enable the user to choose between a full text view 1576 (as currently displayed) or a categorized view 1578 to view studies or protocols grouped by semantic categories. As depicted, the comparison between 1572a and 1572b is based on the inclusion criteria 1573. In some embodiments, the graphical user interface 1570 is displayed in response to a user selecting option 1508 from the main menu (e.g., as shown in FIG. 15A) of the clinical study tool.

FIG. 15H illustrates an example graphical user interface 1580 showing example data driven insights or outputs 1582, 1584, 1586, 1590, and 1592 associated with a clinical study or protocol. The graphical user interface 1580 may enable a user to choose to view these data driven insights 1582, 1584, 1586, 1590, and 1592 for a desired metric by selecting the metric using a dropdown menu 1588. These data driven insights or outputs may include operational burden measures 1582, site burden measures 1584, patient burden measures 1586, historical benchmarks 1590 of the various metrics, and similar historical studies 1592 associated with user inputs. The graphical user interface 1580 may provide or display the historical benchmarks 1590 in the form of a chart containing a predicted value 1591 and other values associated with historical studies for a metric (e.g., time to first patient). The predicted value 1591 may be determined using one of a baseline model or a category-specific ML model selected by the model routing algorithm, as discussed elsewhere herein.

To display the data driven insights 1582, 1584, 1586, 1590, and 1592, the graphical user interface 1580 may receive from a user various inputs 1594, including, for example and without limitation, a study phase 1594a, a therapeutic area 1594b, a type of cancer 1594c, a particular molecule 1594d, a lock date 1594e, and a study type 1594f. Based on the user inputs 1594, values for the plurality of metrics (e.g., enrollment rate, screening rate, patient dropout ratio, screen failure ratio, etc.) may be predicted. For instance, a value for a particular metric may be predicted using one of baseline model or a category-specific ML model selected by the model routing algorithm, as discussed elsewhere herein. Then using the predicted values of the plurality of metrics, operational burden measures 1582, site burden 1584, and patient burden measures 1586 may be calculated. In some embodiments, the graphical user interface 1580 may provide each of the operational burden measures 1582, site burden measures 1584, and patient burden measures 1586 in the form of a score within a min-max range that is indicative of its respective measure, such as a patient burden score 1582a, a site burden score 1584a, and a patient burden score 1586a.

Example Methods

FIG. 16 illustrates an example method 1600 of using model routing in a clinical study tool to predict a plurality of clinical-study metrics for conducting a clinical study. The method 1600 may begin at step 1610, where a user input is received via a graphical user interface of the clinical study tool. The user input may include one or more user selected sub-categories from one or more categories associated with the clinical study for which the user wants a prediction (e.g., data driven insights 414) based on the plurality of clinical-study metrics. For instance, the categories may include phase and TA, where subcategories associated with the phase may include, for example and without limitation, phase 1 study, phase 1b study, phase 2 study, phase 3 study, phase 4 study, etc., and subcategories associated with the TA may include, for example and without limitation, oncology, neurology, orthopedics, ophthalmology, dermatology, cardiology, infectious diseases, etc. By way of an example, the user input received at step 1610 may include phase 1 and oncology subcategories for which the user wants a prediction for a clinical study, as shown in FIG. 3.

At step 1615, a model performance lookup table is retrieved or accessed. In particular embodiments, a call to an API (e.g., prediction API 214) may be made to access or retrieve the model performance lookup table and the various machine learning models, including a baseline model and a plurality of category-specific ML models. The model performance lookup table may include performance benchmarks of the plurality of category-specific ML models with respect to the baseline model in previously predicting the plurality of clinical-study metrics (e.g., enrollment rate, screening rate, screen failure ratio, patient dropout ratio, etc.). In particular embodiments, performance benchmarks are provided in the form of RMSE percent difference from the baseline that indicate performance of each of the category-specific ML models (e.g., phase 1 model, phase 2 model, TA ONC model, etc.) compared to the baseline model in predicting the metrics.

At step 1620, for clinical-study metric of the plurality of clinical-study metrics, an appropriate model is selected from the baseline model and the plurality of category-specific ML models to predict the clinical-study metric using the model performance lookup table. For instance, the model routing algorithm may compare past performances of the baseline model and one or more category-specific ML models associated with the user selected subcategories to determine which model to select to predict the clinical-study metric. If the past performance of the baseline model is better than the one or more category-specific machine-learning models associated with the user selected sub-categories, then the model routing algorithm selects the baseline model for predicting the metric. Otherwise, the model routing algorithm selects a category-specific machine-learning model (e.g., phase 1 model or ONC model) that has the best performance (e.g., highest RMSE percent difference from baseline) in the past in predicting the metric.

At step 1625, a routing dictionary is created based on the selections made in step 1620. The routing dictionary may include a selected model for each of the plurality of metrics for prediction. An example routing dictionary 314 is shown in FIG. 3. At step 1630, values for the plurality of clinical-study metrics are predicted using corresponding selected models according to the routing dictionary. At step 1635, one or more predictions or data driven insights associated with the clinical study are provided for display based on the predicted values for the plurality of clinical-study metrics. In particular embodiments, the one or more predictions or data driven insights associated with the clinical study may include an operational complexity or operational burden measures, patient burden measures, site burden measures, as shown in FIG. 4 or FIG. 15H. In particular embodiments, these data driven insights or predictions for different metrics may be provided on a graphical user interface associated with a clinical study tool, such as ones shown in FIGS. 15D, 15F, and 15H. Users (e.g., clinical scientists) may use these data driven insights or predictions during the protocol design phase to design patient and investigator centric protocols.

Particular embodiments may repeat one or more steps of the method of FIG. 16, where appropriate. Although this disclosure describes and illustrates particular steps of the method of FIG. 16 as occurring in a particular order, this disclosure contemplates any suitable steps of the method of FIG. 16 occurring in any suitable order. Moreover, although this disclosure describes and illustrates an example method of using model routing in a clinical study tool to predict a plurality of clinical-study metrics for conducting a clinical study including the particular steps of the method of FIG. 16, this disclosure contemplates any suitable method of using model routing in a clinical study tool to predict a plurality of clinical-study metrics for conducting a clinical study including any suitable steps, which may include all, some, or none of the steps of the method of FIG. 16, where appropriate. Furthermore, although this disclosure describes and illustrates particular components, devices, or systems carrying out particular steps of the method of FIG. 16, this disclosure contemplates any suitable combination of any suitable components, devices, or systems carrying out any suitable steps of the method of FIG. 16.

FIG. 17 illustrates an example method 1700 for determining an adaptive threshold for outlier detection and removal. The method 1700 begins at step 1710, where a training dataset is received for training one or more machine-learning models. For example, the method 1700 may receive the training dataset 602 for training a baseline model, as shown in FIG. 6. At step 1715, a tolerance or acceptable limit for data loss is set when removing outliers from the training dataset. For instance, the method 1700 may specify that a tolerance or acceptable limit for data loss is less than or equal to 1%. In some embodiments, an automated check may be added for how tuning the data loss percentage affects whether a particular data point remains in the dataset. At step 1715, a threshold-adjustment value is also set by which to adjust a current threshold for removing outliers. For instance, the current threshold may be 3.5 and the threshold-adjustment value may specify an increment value (e.g., 0.5) by which to increment the current threshold at each iteration in an iterative process until an amount of data loss in the training dataset is within the set tolerance or acceptable limit.

At step 1720, a first set of outliers is removed from the training dataset using a first scoring technique (e.g., a standard z-score technique). In particular embodiments, removing the first set of outliers using the first scoring technique may include determining a mean and a standard deviation of the training dataset and calculating, for each data point within the training dataset, a score (e.g., a z-score) based on the mean and standard deviation. The z-score may be calculated using the following formula:

$$Z_i = \frac{Y_i - \overline{Y}}{s}$$

Equation (1)

Where, $\overline{Y}$ and s denote the sample mean and sample standard deviation, respectively. In other words, data is given in units of how many standard deviations it is from the mean.

Data points with scores (e.g., z-scores) with absolute values greater than a predetermined number of standard deviations away from the mean are detected as the first set of outliers. For instance, values with scores (e.g., z-scores) whose absolute values are at least 3 standard deviations above the mean are detected as the first set of outliers. The detected data points or values are then removed from the training dataset. Next, at step 1725, the method 1700 determines and records a first amount of training dataset remaining after the removal of the first set of outliers. For instance, the method 1700 determines how much training data is left after the removal of the data points using the first scoring technique discussed in step 1720.

At step 1730, a second set of outliers is removed from the training dataset (e.g., from training dataset originally received in step 1710) now with a second scoring technique (e.g., a modified z-score technique) and the current threshold (e.g., starts with default baseline threshold of 3.5). In particular embodiments, removing the second set of outliers using the second scoring technique (e.g., modified z-score technique) and the current threshold may include determining a median and a median absolute deviation (MAD) of the training dataset and calculating, for each data point within the training dataset, a score (e.g., a modified z-score) based on the median and the median absolute deviation. The modified z-score may be calculated using the following formula:

$$M_i = \frac{0.6745(x_i - \tilde{x})}{MAD} \qquad \text{Equation (2)}$$

Where, MAD and $\tilde{x}$ denote the median absolute deviation and median, respectively. MAD may be calculated using the following formula:

$$MAD = \text{median}(|Y_i - \tilde{Y}|) \qquad \text{Equation (3)}$$

Where, $\tilde{Y}$ is the median of the data and $|Y|$ is the absolute value of Y. This is a variation of the average absolute deviation that is even less affected by extremes in the tail because the data in the tails have less influence on the calculation of the median than they do on the mean.

Data points with scores (e.g., modified z-scores) with absolute values greater than the current threshold (e.g., baseline threshold of 3.5 at the first iteration) are detected as the second set of outliers and removed from the training dataset. Next, at step 1735, the method 1700 determines and records a second amount of training dataset remaining after the removal of the second set of outliers. For instance, the method 1700 determines how much training data is left after the removal of the data points using the second scoring technique (e.g., modified z-score technique) and the current threshold discussed in step 1730.

At step 1740, an amount of data loss (e.g., percent data loss) is determined by comparing the first amount of training dataset (e.g., obtained from step 1725 based on standard z scores) and the second amount of training dataset (e.g., obtained from step 1735 based on modified z scores and using the current threshold). At step 1745, a determination is made as to whether the amount of data loss (e.g., percent data loss) is greater than the tolerance or acceptable limit that was set in step 1715. For example, the method 1700 may determine whether the percent data loss is greater than the 1% data loss acceptable limit. If the result of the determination of step 1745 is positive, then at step 1750, the current threshold is adjusted by the threshold-adjustment value that was set in step 1715. As an example, the current baseline threshold of 3.5 used at the first iteration is increased by 0.5 and then the steps 1730-1740 are repeated to determine in a subsequent iteration whether the data loss percentage is now within the acceptable tolerance limit. If not, then the threshold is again adjusted (e.g., increased) by the threshold-adjustment value and the process is repeated until the amount of data loss in the training dataset is within the set tolerance limit. Once it is determined that the amount of data loss or percent data loss is within the acceptable tolerance limit or in other words the result of the determination of step 1745 is negative, the iterative process ends and at step 1755, the final adjusted threshold value is used to detect and remove outliers from the training dataset using a particular scoring technique (e.g., a modified z-score technique), as discussed below in reference to FIG. 18.

Particular embodiments may repeat one or more steps of the method of FIG. 17, where appropriate. Although this disclosure describes and illustrates particular steps of the method of FIG. 17 as occurring in a particular order, this disclosure contemplates any suitable steps of the method of FIG. 17 occurring in any suitable order. Moreover, although this disclosure describes and illustrates an example method for determining an adaptive threshold for outlier detection and removal including the particular steps of the method of FIG. 17, this disclosure contemplates any suitable method for determining an adaptive threshold for outlier detection and removal including any suitable steps, which may include all, some, or none of the steps of the method of FIG. 17, where appropriate. Furthermore, although this disclosure describes and illustrates particular components, devices, or systems carrying out particular steps of the method of FIG. 17, this disclosure contemplates any suitable combination of any suitable components, devices, or systems carrying out any suitable steps of the method of FIG. 17.

FIG. 18 illustrates an example method 1800 for outlier detection and removal using the adaptive threshold determined using the method 1700 of FIG. 17. The method 1800 begins at step 1810, where a median of a training dataset of which outliers needs to be removed is determined. At step 1815, a median absolute deviation (MAD) of the training dataset is determined. The MAD may be determined or calculated using the equation (3) above. At step 1820, for each data point within the training dataset, a score (e.g., modified z-score value) is calculated based on the median and the MAD. The modified z-score value may be calculated using the equation (2) above. At step 1825, data points whose scores (e.g., modified z-scores) have absolute values greater than the final adjusted threshold or adaptive threshold (obtained at step 1755 of FIG. 17) are detected as outliers. In some embodiments, the data points or studies that are detected as outliers may be logged to help detect any potential data quality issues that could be fixed on the database side. At step 1830, the detected data points or outliers are removed from the training dataset, as shown for example in FIG. 12. Once the outliers are removed from the training dataset using the methods 1700 and 1800 discussed herein, the training dataset may be used to train various machine learning models, including the baseline model and category-specific ML models, as shown for example in FIG. 6. Once sufficiently trained, these models may be deployed into production (e.g., as shown in FIG. 2) for usage at inference or run time by the model routing algorithm to predict various clinical-study metrics (e.g., as shown in FIG. 3) by intelligently selecting appropriate models for prediction, as discussed elsewhere herein.

Particular embodiments may repeat one or more steps of the method of FIG. 18, where appropriate. Although this disclosure describes and illustrates particular steps of the method of FIG. 18 as occurring in a particular order, this disclosure contemplates any suitable steps of the method of FIG. 18 occurring in any suitable order. Moreover, although this disclosure describes and illustrates an example method for outlier detection and removal using the adaptive threshold including the particular steps of the method of FIG. 18, this disclosure contemplates any suitable method for outlier detection and removal using the adaptive threshold including any suitable steps, which may include all, some, or none of the steps of the method of FIG. 18, where appropriate. Furthermore, although this disclosure describes and illustrates particular components, devices, or systems carrying out particular steps of the method of FIG. 18, this disclosure contemplates any suitable combination of any suitable components, devices, or systems carrying out any suitable steps of the method of FIG. 18.

Figure 19:
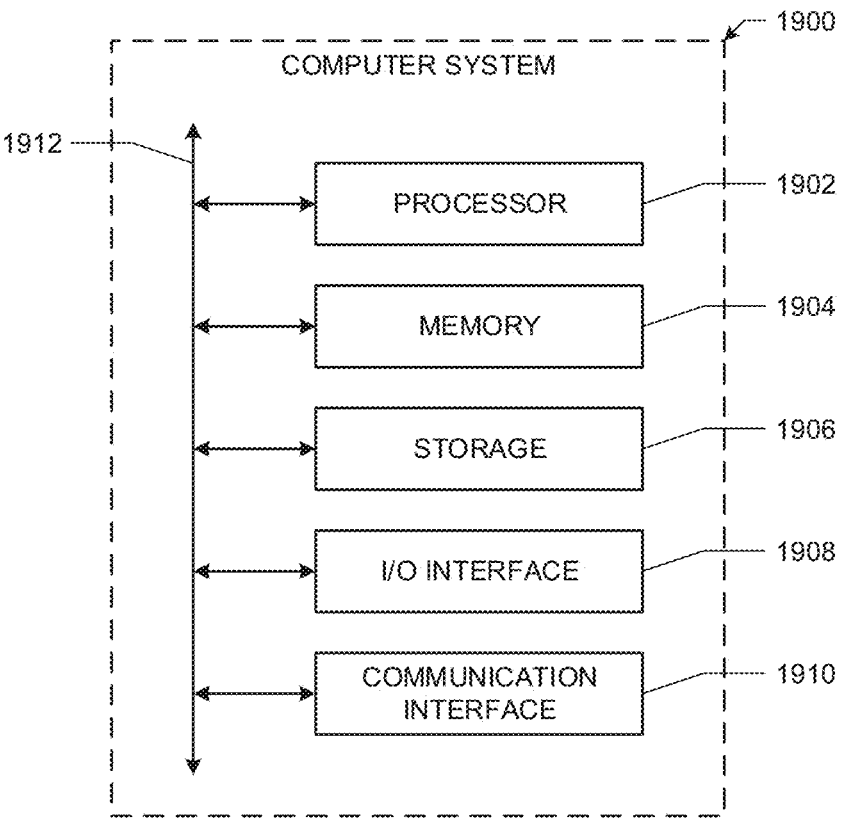
FIG. 19 illustrates an example computer system.

FIG. 19 illustrates an example computer system 1900. In particular embodiments, one or more computer systems 1900 perform one or more steps of one or more methods described or illustrated herein. In particular embodiments, one or more computer systems 1900 provide functionality described or illustrated herein. In particular embodiments, software running on one or more computer systems 1900 performs one or more steps of one or more methods described or illustrated herein or provides functionality described or illustrated herein. Particular embodiments include one or more portions of one or more computer systems 1900. Herein, reference to a computer system may encompass a computing device, and vice versa, where appropriate. Moreover, reference to a computer system may encompass one or more computer systems, where appropriate.

This disclosure contemplates any suitable number of computer systems 1900. This disclosure contemplates computer system 1900 taking any suitable physical form. As example and not by way of limitation, computer system 1900 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, an augmented/virtual reality device, or a combination of two or more of these. Where appropriate, computer system 1900 may include one or more computer systems 1900; be unitary or distributed; span multiple locations; span multiple machines; span multiple data centers; or reside in a cloud, which may include one or more cloud components in one or more networks. Where appropriate, one or more computer systems 1900 may perform without substantial spatial or temporal limitation one or more steps of one or more methods described or illustrated herein. As an example and not by way of limitation, one or more computer systems 1900 may perform in real time or in batch mode one or more steps of one or more methods described or illustrated herein. One or more computer systems 1900 may perform at different times or at different locations one or more steps of one or more methods described or illustrated herein, where appropriate.

In particular embodiments, computer system 1900 includes a processor 1902, memory 1904, storage 1906, an input/output (I/O) interface 1908, a communication interface 1910, and a bus 1912. Although this disclosure describes and illustrates a particular computer system having a particular number of particular components in a particular arrangement, this disclosure contemplates any suitable computer system having any suitable number of any suitable components in any suitable arrangement.

In particular embodiments, processor 1902 includes hardware for executing instructions, such as those making up a computer program. As an example and not by way of limitation, to execute instructions, processor 1902 may retrieve (or fetch) the instructions from an internal register, an internal cache, memory 1904, or storage 1906; decode and execute them; and then write one or more results to an internal register, an internal cache, memory 1904, or storage 1906. In particular embodiments, processor 1902 may include one or more internal caches for data, instructions, or addresses. This disclosure contemplates processor 1902 including any suitable number of any suitable internal caches, where appropriate. As an example and not by way of limitation, processor 1902 may include one or more instruction caches, one or more data caches, and one or more translation lookaside buffers (TLBs). Instructions in the instruction caches may be copies of instructions in memory 1904 or storage 1906, and the instruction caches may speed up retrieval of those instructions by processor 1902. Data in the data caches may be copies of data in memory 1904 or storage 1906 for instructions executing at processor 1902 to operate on; the results of previous instructions executed at processor 1902 for access by subsequent instructions executing at processor 1902 or for writing to memory 1904 or storage 1906; or other suitable data. The data caches may speed up read or write operations by processor 1902. The TLBs may speed up virtual-address translation for processor 1902. In particular embodiments, processor 1902 may include one or more internal registers for data, instructions, or addresses. This disclosure contemplates processor 1902 including any suitable number of any suitable internal registers, where appropriate. Where appropriate, processor 1902 may include one or more arithmetic logic units (ALUs); be a multi-core processor; or include one or more processors 1902. Although this disclosure describes and illustrates a particular processor, this disclosure contemplates any suitable processor.

In particular embodiments, memory 1904 includes main memory for storing instructions for processor 1902 to execute or data for processor 1902 to operate on. As an example and not by way of limitation, computer system 1900 may load instructions from storage 1906 or another source (such as, for example, another computer system 1900) to memory 1904. Processor 1902 may then load the instructions from memory 1904 to an internal register or internal cache. To execute the instructions, processor 1902 may retrieve the instructions from the internal register or internal cache and decode them. During or after execution of the instructions, processor 1902 may write one or more results (which may be intermediate or final results) to the internal register or internal cache. Processor 1902 may then write one or more of those results to memory 1904. In particular embodiments, processor 1902 executes only instructions in one or more internal registers or internal caches or in memory 1904 (as opposed to storage 1906 or elsewhere) and operates only on data in one or more internal registers or internal caches or in memory 1904 (as opposed to storage 1906 or elsewhere). One or more memory buses (which may each include an address bus and a data bus) may couple processor 1902 to memory 1904. Bus 1912 may include one or more memory buses, as described below. In particular embodiments, one or more memory management units (MMUs) reside between processor 1902 and memory 1904 and facilitate accesses to memory 1904 requested by processor 1902. In particular embodiments, memory 1904 includes random access memory (RAM). This RAM may be volatile memory, where appropriate. Where appropriate, this RAM may be dynamic RAM (DRAM) or static RAM (SRAM). Moreover, where appropriate, this RAM may be single-ported or multi-ported RAM. This disclosure contemplates any suitable RAM. Memory 1904 may include one or more memories 1904, where appropriate. Although this disclosure describes and illustrates particular memory, this disclosure contemplates any suitable memory.

In particular embodiments, storage 1906 includes mass storage for data or instructions. As an example and not by way of limitation, storage 1906 may include a hard disk drive (HDD), a floppy disk drive, flash memory, an optical disc, a magneto-optical disc, magnetic tape, or a Universal Serial Bus (USB) drive or a combination of two or more of these. Storage 1906 may include removable or non-removable (or fixed) media, where appropriate. Storage 1906 may be internal or external to computer system 1900, where appropriate. In particular embodiments, storage 1906 is non-volatile, solid-state memory. In particular embodiments, storage 1906 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 1906 taking any suitable physical form. Storage 1906 may include one or more storage control units facilitating communication between processor 1902 and storage 1906, where appropriate. Where appropriate, storage 1906 may include one or more storages 1906. Although this disclosure describes and illustrates particular storage, this disclosure contemplates any suitable storage.

In particular embodiments, I/O interface 1908 includes hardware, software, or both, providing one or more interfaces for communication between computer system 1900 and one or more I/O devices. Computer system 1900 may include one or more of these I/O devices, where appropriate. One or more of these I/O devices may enable communication between a person and computer system 1900. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 1908 for them. Where appropriate, I/O interface 1908 may include one or more device or software drivers enabling processor 1902 to drive one or more of these I/O devices. I/O interface 1908 may include one or more I/O interfaces 1908, where appropriate. Although this disclosure describes and illustrates a particular I/O interface, this disclosure contemplates any suitable I/O interface.

In particular embodiments, communication interface 1910 includes hardware, software, or both providing one or more interfaces for communication (such as, for example, packet-based communication) between computer system 1900 and one or more other computer systems 1900 or one or more networks. As an example and not by way of limitation, communication interface 1910 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 1910 for it. As an example and not by way of limitation, computer system 1900 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 1900 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 1900 may include any suitable communication interface 1910 for any one of these networks, where appropriate. Communication interface 1910 may include one or more communication interfaces 1910, where appropriate. Although this disclosure describes and illustrates a particular communication interface, this disclosure contemplates any suitable communication interface.

In particular embodiments, bus 1912 includes hardware, software, or both coupling components of computer system 1900 to each other. As an example and not by way of limitation, bus 1912 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 1912 may include one or more buses 1912, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any one of these embodiments may include any combination or permutation of any one of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

Various Embodiments

A computer-implemented method for using a clinical study tool to assess a clinical study based on a plurality of clinical-study metrics, the method comprising:
  receiving, via graphical user interface of the clinical study tool, a user input comprising one or more user selected sub-categories from one or more categories associated with the clinical study;
  selecting, for each clinical-study metric of the plurality of clinical-study metrics, a model from either a baseline model or one of a plurality of category-specific machine-learning models to predict the clinical-study metric using a model performance lookup table, the model performance lookup table comprising performance benchmarks of the plurality of category-specific machine-learning models with respect to the baseline model;
  predicting values for the plurality of clinical-study metrics using corresponding selected models;
  generating one or more predictions for assessing the clinical study based on the predicted values for the plurality of clinical-study metrics; and
  displaying, via the graphical user interface of the clinical study tool, the one or more predictions for assessing the clinical study.
The computer-implemented methods for the clinical study tool as recited herein, wherein selecting the model from either the baseline model or one of the plurality of category-specific machine-learning models to predict the clinical-study metric using the model performance lookup table comprises:
  comparing past performances of the baseline model and one or more category-specific machine-learning models associated with the user selected sub-categories in predicting the clinical-study metric;
  determining, based on the comparison, that the past performance of the baseline model is better than the one or more category-specific machine-learning models; and
  in response to the determination, selecting the baseline model for predicting the clinical-study metric.
The computer-implemented methods for the clinical study tool as recited herein, wherein selecting the model from either the baseline model or one of the plurality of category-specific machine-learning models to predict the clinical-study metric using the model performance lookup table comprises:
  comparing past performances of the baseline model and one or more category-specific machine-learning models associated with the user selected sub-categories in predicting the clinical-study metric;
  determining, based on the comparison, that the past performances of the one or more category-specific machine-learning models are better than the baseline model; and in response to the determination, selecting one of the category-specific machine-learning models that has a past performance relatively higher than other category-specific machine-learning models in predicting the clinical-study metric.
The computer-implemented methods for the clinical study tool as recited herein, further comprising training the baseline model and the plurality of category-specific machine-learning models, wherein the training comprises:
  receiving a training dataset comprising ground-truth values for the plurality of clinical-study metrics for the one or more categories;
  filtering the training dataset by each sub-category of the one or more categories to obtain a plurality of category-specific training datasets;
  training the baseline model using the training dataset prior to filtering; and
  training the plurality of category-specific machine-learning models using the plurality of category-specific training datasets.
The computer-implemented methods for the clinical study tool as recited herein, further comprising preparing the model performance lookup table during the training of the baseline model and the plurality of category-specific machine-learning models.
The computer-implemented methods for the clinical study tool as recited herein, wherein preparing the model performance lookup table comprises:
  obtaining predicted values for the plurality of clinical-study metrics by the trained baseline model and the plurality of category-specific machine-learning models;
  comparing the predicted values for the plurality of clinical-study metrics by each model with ground-truth values;
  measuring, for each of the baseline and the plurality of category-specific machine-learning models, differences between the predicted values and the ground-truth values;
  generating a measure of model performance for each category-specific machine-learning model with respect to the baseline model based on the measured differences; and
  storing the measure of model performance for each category-specific machine-learning model with respect to the baseline model in a cell corresponding to each clinical-study metric for each category in the model performance lookup table.
The computer-implemented methods for the clinical study tool as recited herein, further comprising deploying the trained baseline model and the plurality of category-specific machine-learning models for using at inference time for clinical studies, wherein the deploying comprises:
  integrating the trained baseline model and the plurality of category-specific machine-learning models into a container or framework; and
  generating a prediction application programming interface (API) endpoint for the container or framework.
The computer-implemented methods for the clinical study tool as recited herein, further comprising:
  in response to receiving the user input, making a call to the prediction API endpoint.
The computer-implemented methods for the clinical study tool as recited herein, further comprising:
  after deploying the trained baseline model and the plurality of category-specific machine-learning models into production, validating the plurality of category-specific machine-learning models for testing an accuracy in the predictions.

The computer-implemented methods for the clinical study tool as recited herein, wherein validating the plurality of category-specific machine-learning models comprises:

for each clinical-study metric and for each category:

predict the clinical-study metric using the baseline model and a first category-specific machine-learning model associated with the category;

determining an intersection between a test set of the training dataset and a test set of a dataset filtered by the category;

removing a set of samples from an intersected test set for which a model selected for predicting the clinical-study metric is the first category-specific machine-learning model;

training a second baseline model and a plurality of second category-specific machine-learning models using remaining samples in the intersected test set;

predicting the clinical-study metric for the removed set of samples using the second baseline model and the plurality of second category-specific machine-learning models;

comparing the prediction of the clinical-study metric, for each sample, by the first category-specific machine-learning model associated with the category, a second category-specific machine-learning model associated with the category, and the second baseline model;

determining concordance between the first category-specific machine-learning model and the second category-specific machine-learning model based on the comparison; and validating the first category-specific machine-learning model based on the determined concordance.

The computer-implemented methods for the clinical study tool as recited herein, further comprising:

detecting and removing outliers from the training dataset prior to the training of the baseline model and the plurality of category-specific machine-learning models.

The computer-implemented methods for the clinical study tool as recited herein, wherein detecting and removing the outliers from the training dataset:

determining a particular threshold over which to remove the outliers from the training dataset;

determining a median of the training dataset;

determining a median absolute deviation of the training dataset;

calculating, for each data point within the training dataset, a score based on the median and the median absolute deviation;

detecting data points with scores with absolute values greater than the particular threshold as the outliers; and removing the detected data points from the training dataset.

The computer-implemented methods for the clinical study tool as recited herein, wherein determining the particular threshold comprises:

setting (1) a tolerance limit for data loss when removing outliers from the training dataset and (2) a threshold-adjustment value by which to adjust a current threshold for removing the outliers;

removing a first set of outliers from the training dataset using a first scoring technique;

determining a first amount of training dataset remaining after the removal of the first set of outliers;

determining, through an iterative process, a final adjusted threshold for removing the outliers from the training dataset, wherein an initial iteration in the iterative process comprises:

removing a second set of outliers from the training dataset using a second scoring technique and the current threshold;

determining a second amount of training dataset remaining after the removal of the second set of outliers;

determining an amount of data loss in the training dataset by comparing the first amount of training dataset and the second amount of training dataset; and adjusting the current threshold by the threshold-adjustment value if the determined amount of data loss is greater than the set tolerance limit for data loss; and using the final adjusted threshold as the particular threshold for removing the outliers from the training dataset.

The computer-implemented methods for the clinical study tool as recited herein, wherein the one or more predictions for assessing the clinical study comprises:

operational burden measures;

patient burden measures; or site burden measures.

The computer-implemented methods for the clinical study tool as recited herein, wherein a clinical-study metric of the plurality of clinical-study metrics is one of:

an enrollment rate of patients;

a screening rate of patients;

a screen failure ratio;

a patient dropout ratio;

time to regulatory approval;

time to enrollment completion;

time to first patient enrollment;

protocol deviations per patient; or number of unique procedures in the clinical study.

The computer-implemented methods for the clinical study tool as recited herein, wherein the one or more categories comprise:

a first category comprising different phases of a clinical trial or the clinical study; and a second category comprising different therapeutic areas in the clinical study.

The computer-implemented methods for the clinical study tool as recited herein, wherein each subcategory of the first category is one of the different phases of the clinical trial.

The computer-implemented methods for the clinical study tool as recited herein, wherein each subcategory of the second category is one of the therapeutic areas in the clinical study.

A computer-program product tangibly embodied in a non-transitory machine-readable storage medium, including instructions configured to cause one or more data processors to perform part or all of one or more of the computer-implemented methods for the clinical study tool as recited herein.

A system comprising:

one or more processors; and a non-transitory computer readable storage medium containing instructions which, when executed on the one or more data processors, cause the one or more data processors to perform part or all of one or more of the computer-implemented methods for the clinical study tool as recited herein.

A computer-implemented method for removing outliers comprising:

receiving a training dataset for training one or more machine-learning models;

setting (1) a tolerance limit for data loss when removing outliers from the training dataset and (2) a threshold-adjustment value by which to adjust a current threshold for removing the outliers;

removing a first set of outliers from the training dataset using a first scoring technique;

determining a first amount of training dataset remaining after the removal of the first set of outliers;

determining, through an iterative process, a final adjusted threshold for removing the outliers from the training dataset, wherein an initial iteration in the iterative process comprises:

removing a second set of outliers from the training dataset using a second scoring technique and the current threshold;

determining a second amount of training dataset remaining after the removal of the second set of outliers;

determining an amount of data loss in the training dataset by comparing the first amount of training dataset and the second amount of training dataset; and adjusting the current threshold by the threshold-adjustment value if the determined amount of data loss is greater than the set tolerance limit for data loss; and detecting and removing the outliers from the training dataset using the final adjusted threshold value.

The computer-implemented methods for removing outliers as recited herein, wherein one or more subsequent iterations in the iterative process are performed until the amount of data loss in the training dataset is within the set tolerance limit.

The computer-implemented methods for removing outliers as recited herein, wherein the threshold-adjustment value is an increment value by which to increment the current threshold at each iteration in the iterative process until the amount of data loss in the training dataset is within the set tolerance limit.

The computer-implemented methods for removing outliers as recited herein, wherein detecting and removing the outliers from the training dataset comprises:

determining a median of the training dataset;

determining a median absolute deviation of the training dataset;

calculating, for each data point within the training dataset, a score based on the median and the median absolute deviation;

detecting data points with scores with absolute values greater than the final adjusted threshold as the outliers; and removing the detected data points from the training dataset.

The computer-implemented methods for removing outliers as recited herein, wherein removing the first set of outliers from the training dataset using the first scoring technique comprises:

determining a mean of the training dataset;

determining a standard deviation of the training dataset;

calculating, for each data point within the training dataset, a score based on the mean and the standard deviation;

detecting data points with scores with absolute values greater than a predetermined number of standard deviations away from the mean as the first set of outliers; and removing the detected data points from the training dataset.

The computer-implemented methods for removing outliers as recited herein, wherein removing the second set of outliers from the training dataset using the second scoring technique and the current threshold comprises:

determining a median of the training dataset;

determining a median absolute deviation of the training dataset;

calculating, for each data point within the training dataset, a score based on the median and the median absolute deviation;

detecting data points with scores with absolute values greater than the current threshold as the second set of outliers; and removing the detected data points from the training dataset.

The computer-implemented methods for removing outliers as recited herein, wherein:

the first scoring technique is a standard z-score technique; and the second scoring technique is a modified z-score technique.

The computer-implemented methods for removing outliers as recited herein, further comprising:

identifying data points associated with detected outliers; and logging the identified data points, wherein the logged data points are used to detect potential data quality issues.

The computer-implemented methods for removing outliers as recited herein, further comprising:

adding an automated check that determines an effect of the set tolerance limit on the presence of one or more data points within the training dataset.

The computer-implemented methods for removing outliers as recited herein, wherein the one or more machine-learning models comprise a baseline model and one or more category-specific machine-learning models.

The computer-implemented methods for removing outliers as recited herein, further comprising:

after detecting and removing the outliers from the training dataset, training the baseline model and the one or more category-specific machine-learning models using the training dataset.

The computer-implemented methods for removing outliers as recited herein, wherein training the baseline model and the one or more category-specific machine-learning models comprises:

filtering the training dataset by one or more categories associated with a clinical study to obtain one or more category-specific training datasets;

training the baseline model using the training dataset prior to filtering; and training the one or more category-specific machine-learning models using the one or more category-specific training datasets.

The computer-implemented methods for removing outliers as recited herein, wherein the one or more categories comprise:

a first category comprising different phases of the clinical study or a clinical trial; and a second category comprising different therapeutic areas in the clinical study.

The computer-implemented methods for removing outliers as recited herein, further comprising preparing a model performance lookup table during the training of the baseline model and the one or more category-specific machine-learning models, wherein the model performance lookup table comprises performance benchmarks of the one or more category-specific machine-learning models with respect to the baseline model in predicting a plurality of clinical-study metrics.

The computer-implemented methods for removing outliers as recited herein, wherein preparing the model performance lookup table comprises:

obtaining predicted values for the plurality of clinical-study metrics by the trained baseline model and the one or more category-specific machine-learning models;

comparing the predicted values for the plurality of clinical-study metrics by each model with ground-truth values;

measuring, for each of the baseline and the one or more category-specific machine-learning models, differences between the predicted values and the ground-truth values;

generating a measure of model performance for each category-specific machine-learning model with respect to the baseline model based on the measured differences; and storing the measure of model performance for each category-specific machine-learning model with respect to the baseline model in a cell corresponding to each clinical-study metric for each category in the model performance lookup table.

The computer-implemented methods for removing outliers as recited herein, wherein the training dataset comprises ground-truth values for a particular clinical-study metric of the plurality of clinical-study metrics for the one or more categories associated with the clinical study.

The computer-implemented methods for removing outliers as recited herein, wherein a threshold value for removing outliers from a training dataset associated with each clinical-study metric of the plurality of clinical-study metrics is different.

The computer-implemented methods for removing outliers as recited herein, wherein a clinical-study metric of the plurality of clinical-study metrics is one of:

an enrollment rate of patients;

a screening rate of patients;

a screen failure ratio;

a patient dropout ratio;

time to regulatory approval;

time to enrollment completion;

time to first patient enrollment;

protocol deviations per patient; or number of unique procedures in the clinical study.

A computer-program product tangibly embodied in a non-transitory machine-readable storage medium, including instructions configured to cause one or more data processors to perform part or all of one or more of the computer-implemented methods for removing outliers as recited herein.

A system comprising:

one or more processors; and a non-transitory computer readable storage medium containing instructions which, when executed on the one or more data processors, cause the one or more data processors to perform part or all of one or more of the computer-implemented methods for removing outliers as recited herein.

What is claimed is:

1. A computer-implemented method for using a clinical study tool to assess a clinical study based on a plurality of clinical-study metrics, the method comprising:

receiving, via graphical user interface of the clinical study tool, a user input comprising one or more user selected sub-categories from one or more categories associated with the clinical study;

obtaining a model performance lookup table comprising performance benchmarks for each of a plurality of category-specific machine-learning models with respect to a baseline machine-learning model, wherein the model performance lookup table is generated by:

obtaining test inputs and corresponding ground-truth values for one or more clinical-study metrics;

evaluating, based on the test inputs and the corresponding ground-truth values, the baseline machine-learning model and the plurality of category-specific machine-learning models; and generating the performance benchmarks based on the evaluation;

selecting, for each clinical-study metric of the plurality of clinical-study metrics, a model from a set of machine-learning models comprising the baseline machine-learning model and the plurality of category-specific machine-learning models wherein the selection is based on the model performance lookup table;

predicting values for the plurality of clinical-study metrics using corresponding selected models;

generating one or more predictions for assessing the clinical study based on the predicted values for the plurality of clinical-study metrics; and displaying, via the graphical user interface of the clinical study tool, the one or more predictions for assessing the clinical study.

2. The method of claim 1, wherein selecting the model from either the baseline machine-learning model or one of the plurality of category-specific machine-learning models to predict the clinical-study metric using the model performance lookup table comprises:

comparing past performances of the baseline machine-learning model and one or more category-specific machine-learning models associated with the user selected sub-categories in predicting the clinical-study metric;

determining, based on the comparison, that the past performance of the baseline machine-learning model is better than the one or more category-specific machine-learning models; and in response to the determination, selecting the baseline machine-learning model for predicting the clinical-study metric.

3. The method of claim 1, wherein selecting the model from either the baseline machine-learning model or one of the plurality of category-specific machine-learning models to predict the clinical-study metric using the model performance lookup table comprises:

comparing past performances of the baseline machine-learning model and one or more category-specific machine-learning models associated with the user selected sub-categories in predicting the clinical-study metric;

determining, based on the comparison, that the past performances of the one or more category-specific machine-learning models are better than the baseline machine-learning model; and in response to the determination, selecting one of the category-specific machine-learning models that has a past performance relatively higher than other category-specific machine-learning models in predicting the clinical-study metric.

4. The method of claim 1, further comprising training the baseline machine-learning model and the plurality of category-specific machine-learning models, wherein the training comprises:

receiving a training dataset comprising ground-truth values for the plurality of clinical-study metrics for the one or more categories;

filtering the training dataset by each sub-category of the one or more categories to obtain a plurality of category-specific training datasets;

training the baseline machine-learning model using the training dataset prior to filtering; and training the plurality of category-specific machine-learning models using the plurality of category-specific training datasets.

5. The method of claim 4, wherein the model performance lookup table is generated after training of the baseline machine-learning model and the plurality of category-specific machine-learning models.

6. The method of claim 4, further comprising deploying the trained baseline machine-learning model and the plurality of category-specific machine-learning models for using at inference time for clinical studies, wherein the deploying comprises:

integrating the trained baseline machine-learning model and the plurality of category-specific machine-learning models into a container or framework; and generating a prediction application programming interface (API) endpoint for the container or framework.

7. The method of claim 6, further comprising:

in response to receiving the user input, making a call to the prediction API endpoint.

8. The method of claim 6, further comprising:

after deploying the trained baseline machine-learning model and the plurality of category-specific machine-learning models into production, validating the plurality of category-specific machine-learning models for testing an accuracy in the predictions.

9. The method of claim 8, wherein validating the plurality of category-specific machine-learning models comprises:

for each clinical-study metric and for each category:

predicting the clinical-study metric using the baseline machine-learning model and a first category-specific machine-learning model associated with the category;

determining an intersection between a test set of the training dataset and a test set of a dataset filtered by the category;

removing a set of samples from an intersected test set for which a model selected for predicting the clinical-study metric is the first category-specific machine-learning model;

training a second baseline machine-learning model and a plurality of second category-specific machine-learning models using remaining samples in the intersected test set;

predicting the clinical-study metric for the removed set of samples using the second baseline machine-learning model and the plurality of second category-specific machine-learning models;

comparing the prediction of the clinical-study metric, for each sample, by the first category-specific machine-learning model associated with the category, a second category-specific machine-learning model associated with the category, and the second baseline machine-learning model;

determining concordance between the first category-specific machine-learning model and the second category-specific machine-learning model based on the comparison; and validating the first category-specific machine-learning model based on the determined concordance.

10. The method of claim 4, further comprising:

detecting and removing outliers from the training dataset prior to the training of the baseline machine-learning model and the plurality of category-specific machine-learning models.

11. The method of claim 10, wherein detecting and removing the outliers from the training dataset:

determining a particular threshold over which to remove the outliers from the training dataset;

determining a median of the training dataset;

determining a median absolute deviation of the training dataset;

calculating, for each data point within the training dataset, a score based on the median and the median absolute deviation;

detecting data points with scores with absolute values greater than the particular threshold as the outliers; and removing the detected data points from the training dataset.

12. The method of claim 11, wherein determining the particular threshold comprises:

setting (1) a tolerance limit for data loss when removing the outliers from the training dataset and (2) a threshold-adjustment value by which to adjust a current threshold for removing the outliers;

removing a first set of outliers from the training dataset using a first scoring technique;

determining a first amount of the training dataset remaining after the removal of the first set of outliers;

determining, through an iterative process, a final adjusted threshold for removing the outliers from the training dataset, wherein an initial iteration in the iterative process comprises:

removing a second set of outliers from the training dataset using a second scoring technique and the current threshold;

determining a second amount of the training dataset remaining after the removal of the second set of outliers;

determining an amount of data loss in the training dataset by comparing the first amount of the training dataset and the second amount of the training dataset; and adjusting the current threshold by the threshold-adjustment value if the determined amount of data loss is greater than the set tolerance limit for data loss; and using the final adjusted threshold as the particular threshold for removing the outliers from the training dataset.

13. The method of claim 1, wherein evaluating, based on the test inputs and the corresponding ground-truth values, the baseline machine-learning model and the category-specific machine-learning models comprises:

obtaining, using the test inputs, predicted values for the plurality of clinical-study metrics by the baseline machine-learning model and the plurality of category-specific machine-learning models;

comparing the predicted values for the plurality of clinical-study metrics by each model with the corresponding ground-truth values; and measuring, for each of the baseline machine-learning model and the plurality of category-specific machine-learning models, differences between the predicted values and the corresponding ground-truth values; and wherein generating the performance benchmarks based on the evaluation comprises:

generating a measure of model performance for each category-specific machine-learning model with respect to the baseline machine-learning model based on the measured differences; and storing the measure of model performance for each category-specific machine-learning model with respect to the baseline machine-learning model in a cell corresponding to each clinical-study metric for each category in the model performance lookup table.

14. The method of claim 1, wherein the one or more predictions for assessing the clinical study comprises:

operational burden measures;

patient burden measures; or site burden measures.

15. The method of claim 1, wherein a clinical-study metric of the plurality of clinical-study metrics is one of:

an enrollment rate of patients;

a screening rate of patients;

a screen failure ratio;

a patient dropout ratio;

time to regulatory approval;

time to enrollment completion;

time to first patient enrollment;

protocol deviations per patient; or number of unique procedures in the clinical study.

16. The method of claim 1, wherein the one or more categories comprise:

a first category comprising different phases of a clinical trial or the clinical study; and a second category comprising different therapeutic areas in the clinical study.

17. The method of claim 16, wherein each subcategory of the first category is one of the different phases of the clinical trial.

18. The method of claim 16, wherein each subcategory of the second category is one of the therapeutic areas in the clinical study.

19. A computer-program product for using a clinical study tool to assess a clinical study based on a plurality of clinical-study metrics, the computer-program product tangibly embodied in a non-transitory machine-readable storage medium, including instructions configured to cause one or more data processors to:

receive, via graphical user interface of the clinical study tool, a user input comprising one or more user selected sub-categories from one or more categories associated with the clinical study;

obtain a model performance lookup table comprising performance benchmarks for each of a plurality of category-specific machine-learning models with respect to a baseline machine-learning model, wherein the model performance lookup table is generated by:

obtaining test inputs and corresponding ground-truth values for one or more clinical-study metrics;

evaluating, based on the test inputs and the corresponding ground-truth values, the baseline machine-learning model and category-specific machine-learning models; and generating the performance benchmarks based on the evaluation;

select, for each clinical-study metric of the plurality of clinical-study metrics, a model from a set of machine-learning models comprising the baseline machine-learning model and the plurality of category-specific machine-learning models wherein the selection is based on the model performance lookup table;

predict values for the plurality of clinical-study metrics using corresponding selected models;

generate one or more predictions for assessing the clinical study based on the predicted values for the plurality of clinical-study metrics; and display, via the graphical user interface of the clinical study tool, the one or more predictions for assessing the clinical study.

20. A system for using a clinical study tool to assess a clinical study based on a plurality of clinical-study metrics, comprising:

one or more processors; and a non-transitory computer readable storage medium containing instructions which, when executed on the one or more processors, cause the one or more processors to:

receive, via graphical user interface of the clinical study tool, a user input comprising one or more user selected sub-categories from one or more categories associated with the clinical study;

obtain a model performance lookup table comprising performance benchmarks for each of a plurality of category-specific machine-learning models with respect to a baseline machine-learning model, wherein the model performance lookup table is generated by:

obtaining test inputs and corresponding ground-truth values for one or more clinical-study metrics;

evaluating, based on the test inputs and the corresponding ground-truth values, the baseline machine-learning model and category-specific machine-learning models; and generating the performance benchmarks based on the evaluation;

select, for each clinical-study metric of the plurality of clinical-study metrics, a model from a set of machine-learning models comprising the baseline machine-learning model and the plurality of category-specific machine-learning models wherein the selection is based on the model performance lookup table;

predict values for the plurality of clinical-study metrics using corresponding selected models;

generate one or more predictions for assessing the clinical study based on the predicted values for the plurality of clinical-study metrics; and display, via the graphical user interface of the clinical study tool, the one or more predictions for assessing the clinical study.

* * * * *